(12) United States Patent
Palanker et al.

(10) Patent No.: US 7,736,361 B2
(45) Date of Patent: Jun. 15, 2010

(54) ELECTROSURGICAL SYSTEM WITH UNIFORMLY ENHANCED ELECTRIC FIELD AND MINIMAL COLLATERAL DAMAGE

(75) Inventors: Daniel V. Palanker, Sunnyvale, CA (US); Alexander B. Vankov, Menlo Park, CA (US)

(73) Assignee: The Board of Trustees of the Leland Stamford Junior University, Palo Alto, CA (US)

( * ) Notice: Subject to any disclaimer, the term of this patent is extended or adjusted under 35 U.S.C. 154(b) by 8 days.

(21) Appl. No.: 11/787,500

(22) Filed: Apr. 16, 2007

(65) Prior Publication Data
US 2008/0027428 A1   Jan. 31, 2008

(51) Int. Cl.
*A61B 18/14*   (2006.01)
(52) U.S. Cl. ........................................................ 606/45
(58) Field of Classification Search .............. 606/32–50
See application file for complete search history.

(56) References Cited

U.S. PATENT DOCUMENTS

| 3,799,168 A | 3/1974 | Peters |
| 3,903,891 A | 9/1975 | Brayshaw |
| 3,970,088 A | 7/1976 | Morrison |
| 3,987,795 A | 10/1976 | Morrison |
| 4,034,762 A | 7/1977 | Cosen |
| 4,043,342 A | 8/1977 | Morrison, Jr. |
| 4,074,718 A | 2/1978 | Morrison, Jr. |
| 4,161,950 A | 7/1979 | Doss et al. |
| 4,202,337 A | 5/1980 | Hren et al. |
| 4,228,800 A | 10/1980 | Degler, Jr. et al. |
| 4,248,231 A | 2/1981 | Herczog et al. |
| 4,429,694 A | 2/1984 | McGreevy |
| 4,476,862 A | 10/1984 | Pao |
| 4,492,231 A | 1/1985 | Auth |
| 4,534,347 A | 8/1985 | Taylor |
| 4,559,943 A | 12/1985 | Bowers |
| 4,589,411 A | 5/1986 | Friedman |
| 4,590,934 A | 5/1986 | Malis et al. |

(Continued)

FOREIGN PATENT DOCUMENTS

EP       0 012 037 A1    6/1980

(Continued)

OTHER PUBLICATIONS

Jones, H.M. et al. (Jan. 15, 1995). "Pulsed Dielectric Breakdown of Pressurized Water and Salt Solutions," *J. Appl. Phys.* 77(2):795-805.

(Continued)

*Primary Examiner*—Michael Peffley
*Assistant Examiner*—Ronald Hupczey, Jr.
(74) *Attorney, Agent, or Firm*—Morrison & Foerster LLP

(57) ABSTRACT

The present invention is directed towards an electrosurgical cutting system. The system comprises an electrically conductive blade, having an uninsulated cutting edge that is surrounded by an insulator. A source of pulsed electrical energy may be coupled to the electrically conductive blade to provide a substantially uniform and highly enhanced electric field along a cutting portion of the blade edge. The blade may have a uniform rate of erosion during use, so that both the conductive metal edge and the surrounding insulation layer erode at approximately the same rate. Also described are methods of fabricating insulated cutting electrodes, particularly blade electrodes.

27 Claims, 20 Drawing Sheets

U.S. PATENT DOCUMENTS

| | | | |
|---|---|---|---|
| 4,593,691 | A | 6/1986 | Lindstrom et al. |
| 4,597,388 | A | 7/1986 | Koziol et al. |
| 4,655,215 | A | 4/1987 | Pike |
| 4,674,499 | A | 6/1987 | Pao |
| 4,781,175 | A | 11/1988 | McGreevy et al. |
| 4,805,616 | A | 2/1989 | Pao |
| 4,901,709 | A | 2/1990 | Rattner et al. |
| 4,927,420 | A | 5/1990 | Newkirk et al. |
| 4,936,301 | A | 6/1990 | Rexroth et al. |
| 4,938,761 | A | 7/1990 | Enssllin |
| 4,943,290 | A | 7/1990 | Rexroth et al. |
| 5,080,660 | A | 1/1992 | Buelna |
| 5,088,997 | A | 2/1992 | Delahuerga et al. |
| 5,108,391 | A | 4/1992 | Flachenecker et al. |
| 5,217,457 | A | 6/1993 | Delahuerga et al. |
| 5,254,121 | A | 10/1993 | Manevitz et al. |
| 5,267,994 | A | 12/1993 | Gentelia et al. |
| 5,281,216 | A | 1/1994 | Klicek |
| 5,300,068 | A | 4/1994 | Rosar et al. |
| 5,318,563 | A | 6/1994 | Malis et al. |
| 5,348,553 | A | 9/1994 | Whitney |
| 5,423,814 | A | 6/1995 | Zhu et al. |
| 5,454,809 | A | 10/1995 | Janssen |
| 5,496,314 | A | 3/1996 | Eggers |
| 5,549,604 | A | 8/1996 | Sutcu et al. |
| 5,569,242 | A | 10/1996 | Lax et al. |
| 5,599,346 | A | 2/1997 | Edwards et al. |
| 5,647,871 | A | 7/1997 | Levine et al. |
| 5,658,279 | A | 8/1997 | Nardella et al. |
| 5,669,904 | A | 9/1997 | Platt, Jr. et al. |
| 5,683,366 | A | 11/1997 | Eggers et al. |
| 5,697,281 | A | 12/1997 | Eggers et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,700,262 | A | 12/1997 | Acosta et al. |
| 5,766,153 | A | 6/1998 | Eggers et al. |
| 5,766,170 | A | 6/1998 | Eggers |
| 5,785,704 | A | 7/1998 | Bille et al. |
| 5,843,019 | A | 12/1998 | Eggers et al. |
| 5,860,976 | A | 1/1999 | Billings et al. |
| 5,873,855 | A | 2/1999 | Eggers et al. |
| 5,891,095 | A | 4/1999 | Eggers et al. |
| 5,891,142 | A | 4/1999 | Eggers et al. |
| 5,958,266 | A | 9/1999 | Fugo et al. |
| 6,004,319 | A | 12/1999 | Goble et al. |
| 6,032,674 | A | 3/2000 | Eggers et al. |
| 6,047,700 | A | 4/2000 | Eggers et al. |
| 6,053,172 | A | 4/2000 | Hovda et al. |
| 6,056,746 | A | 5/2000 | Goble et al. |
| 6,059,782 | A | 5/2000 | Novak et al. |
| 6,059,783 | A | 5/2000 | Kirwan, Jr. |
| 6,066,134 | A | 5/2000 | Eggers et al. |
| 6,066,137 | A | 5/2000 | Greep |
| 6,102,046 | A | 8/2000 | Weinstein et al. |
| 6,113,594 | A | 9/2000 | Savage |
| 6,132,427 | A | 10/2000 | Jones et al. |
| 6,135,998 | A | 10/2000 | Palanker |
| 6,149,620 | A | 11/2000 | Baker et al. |
| 6,149,646 | A | 11/2000 | West, Jr. et al. |
| 6,165,175 | A | 12/2000 | Wampler et al. |
| 6,174,309 | B1 | 1/2001 | Wrublewski et al. |
| 6,183,469 | B1 | 2/2001 | Thapliyal et al. |
| 6,190,381 | B1 | 2/2001 | Olsen et al. |
| 6,210,404 | B1 | 4/2001 | Shadduck |
| 6,228,081 | B1 | 5/2001 | Goble |
| 6,228,082 | B1 | 5/2001 | Baker et al. |
| 6,228,084 | B1 | 5/2001 | Kirwan, Jr. |
| 6,254,600 | B1 | 7/2001 | Willink et al. |
| 6,267,757 | B1 | 7/2001 | Aita et al. |
| 6,287,305 | B1 | 9/2001 | Heim et al. |
| 6,287,306 | B1 | 9/2001 | Kroll et al. |
| 6,352,535 | B1 | 3/2002 | Lewis et al. |
| 6,355,032 | B1 | 3/2002 | Hovda et al. |
| 6,358,248 | B1 | 3/2002 | Mulier et al. |
| 6,364,877 | B1 | 4/2002 | Goble et al. |
| 6,398,779 | B1 | 6/2002 | Buysse et al. |
| 6,447,511 | B1 | 9/2002 | Slater |
| 6,458,121 | B1 | 10/2002 | Rosenstock et al. |
| 6,478,794 | B1 | 11/2002 | Trapp et al. |
| 6,479,785 | B1 | 11/2002 | Fugo et al. |
| 6,482,201 | B1 | 11/2002 | Olsen et al. |
| 6,482,205 | B1 | 11/2002 | Bonnet |
| 6,500,176 | B1 | 12/2002 | Truckai et al. |
| 6,530,924 | B1 | 3/2003 | Ellman et al. |
| 6,533,781 | B2 | 3/2003 | Heim et al. |
| 6,544,261 | B2 | 4/2003 | Ellsberry et al. |
| 6,589,237 | B2 | 7/2003 | Woloszko et al. |
| 6,620,160 | B2 | 9/2003 | Lewis et al. |
| 6,679,269 | B2 | 1/2004 | Swanson |
| 6,726,683 | B1 | 4/2004 | Shaw |
| 6,749,608 | B2 | 6/2004 | Garito et al. |
| 6,770,071 | B2 | 8/2004 | Woloszko et al. |
| 6,780,178 | B2 | 8/2004 | Palanker et al. |
| 6,787,730 | B2 | 9/2004 | Coccio et al. |
| 6,802,842 | B2 | 10/2004 | Ellman et al. |
| 6,818,102 | B1 | 11/2004 | Viol |
| 6,837,887 | B2 | 1/2005 | Woloszko et al. |
| 6,949,096 | B2 | 9/2005 | Davison et al. |
| 6,960,204 | B2 | 11/2005 | Eggers et al. |
| 6,991,631 | B2 | 1/2006 | Woloszko et al. |
| 7,004,941 | B2 | 2/2006 | Tvinnereim et al. |
| 7,090,672 | B2 | 8/2006 | Underwood et al. |
| 7,094,215 | B2 | 8/2006 | Davison et al. |
| RE39,358 | E | 10/2006 | Goble |
| 7,115,139 | B2 | 10/2006 | McClurken et al. |
| 7,131,969 | B1 | 11/2006 | Hovda et al. |
| 7,169,143 | B2 | 1/2007 | Eggers et al. |
| 7,179,255 | B2 | 2/2007 | Lettice et al. |
| 7,182,762 | B2 | 2/2007 | Bortkiewicz |
| 7,186,234 | B2 | 3/2007 | Dahla et al. |
| 7,192,428 | B2 | 3/2007 | Eggers et al. |
| 7,195,627 | B2 | 3/2007 | Amoah et al. |
| 7,195,630 | B2 | 3/2007 | Ciarrocca |
| 7,201,750 | B1 | 4/2007 | Eggers et al. |
| 7,238,185 | B2 | 7/2007 | Palanker et al. |
| 7,270,658 | B2 | 9/2007 | Woloszko et al. |
| 7,720,661 | | 9/2007 | Dahla et al. |
| 7,276,063 | B2 | 10/2007 | Davison et al. |
| 7,429,262 | B2 | 9/2008 | Woloszko et al. |
| 7,435,247 | B2 | 10/2008 | Woloszko et al. |
| 7,445,618 | B2 | 11/2008 | Eggers et al. |
| 7,468,059 | B2 | 12/2008 | Eggers et al. |
| 2001/0012934 | A1 | 8/2001 | Chandrasekaran et al. |
| 2001/0034519 | A1 | 10/2001 | Goble et al. |
| 2002/0052599 | A1 | 5/2002 | Goble et al. |
| 2002/0052600 | A1 | 5/2002 | Davison et al. |
| 2004/0162554 | A1 | 8/2004 | Lee et al. |
| 2004/0199157 | A1 | 10/2004 | Palanker et al. |
| 2004/0236321 | A1 | 11/2004 | Palanker et al. |
| 2004/0267254 | A1 | 12/2004 | Manzo et al. |
| 2005/0021028 | A1 | 1/2005 | Palanker et al. |
| 2005/0220674 | A1 | 10/2005 | Shafirstein et al. |
| 2005/0234439 | A1 | 10/2005 | Underwood |
| 2005/0234446 | A1 | 10/2005 | Van Wyk et al. |
| 2005/0288665 | A1 | 12/2005 | Woloszko |
| 2006/0069386 | A1 | 3/2006 | Dubnack et al. |
| 2006/0155270 | A1 | 7/2006 | Hancock et al. |
| 2006/0253117 | A1 | 11/2006 | Hovda et al. |
| 2006/0259025 | A1 | 11/2006 | Dahla |
| 2006/0259033 | A1 | 11/2006 | Nesbitt |
| 2007/0112348 | A1 | 5/2007 | Eggers et al. |
| 2007/0129715 | A1 | 6/2007 | Eggers et al. |
| 2007/0149966 | A1 | 6/2007 | Dahla et al. |

| | | | |
|---|---|---|---|
| 2007/0179497 A1 | 8/2007 | Eggers et al. | |
| 2007/0239156 A1 | 10/2007 | Palanker et al. | |
| 2008/0004621 A1 | 1/2008 | Dahla et al. | |
| 2008/0015565 A1 | 1/2008 | Davison | |
| 2008/0021447 A1 | 1/2008 | Davison | |
| 2008/0039832 A1 | 2/2008 | Palanker et al. | |
| 2008/0119842 A1 | 5/2008 | Palanker et al. | |
| 2008/0125774 A1 | 5/2008 | Palanker et al. | |

FOREIGN PATENT DOCUMENTS

| | | |
|---|---|---|
| EP | 0 672 841 A2 | 9/1995 |
| EP | 0 672 841 A3 | 9/1995 |
| EP | 0 672 841 B1 | 9/1995 |
| EP | 0 694 290 B1 | 1/1996 |
| EP | 0 697 841 B1 | 2/1996 |
| EP | 0 697 841 B2 | 2/1996 |
| EP | 0 708 618 B1 | 5/1996 |
| EP | 0 754 437 A3 | 1/1997 |
| EP | 0 754 437 B1 | 1/1997 |
| EP | 0 754 437 B2 | 1/1997 |
| EP | 0 771 176 B1 | 5/1997 |
| EP | 0 771 176 B2 | 5/1997 |
| EP | 0 820 249 B1 | 1/1998 |
| EP | 0 833 593 B1 | 4/1998 |
| EP | 0 833 593 B2 | 4/1998 |
| EP | 0 837 647 B1 | 4/1998 |
| EP | 0 858 295 B1 | 8/1998 |
| EP | 0 865 256 B1 | 9/1998 |
| EP | 0 869 742 B1 | 10/1998 |
| EP | 0 873 089 B1 | 10/1998 |
| EP | 0 882 430 A3 | 12/1998 |
| EP | 0 882 430 B1 | 12/1998 |
| EP | 0 886 493 B1 | 12/1998 |
| EP | 0 887 046 B1 | 12/1998 |
| EP | 0 923 907 A1 | 6/1999 |
| EP | 0 949 886 B1 | 10/1999 |
| EP | 0 959 784 B1 | 12/1999 |
| EP | 0 959 786 B1 | 12/1999 |
| EP | 0 959 787 B1 | 12/1999 |
| EP | 0 996 378 B1 | 5/2000 |
| EP | 1 018 994 B1 | 7/2000 |
| EP | 1 025 807 A3 | 8/2000 |
| EP | 1 025 807 B1 | 8/2000 |
| EP | 1 026 996 B1 | 8/2000 |
| EP | 1 027 020 B1 | 8/2000 |
| EP | 1 034 746 A3 | 9/2000 |
| EP | 1 034 746 B1 | 9/2000 |
| EP | 1 034 747 A1 | 9/2000 |
| EP | 1 034 748 A1 | 9/2000 |
| EP | 1 036 547 A2 | 9/2000 |
| EP | 1 036 547 A3 | 9/2000 |
| EP | 1 039 862 B1 | 10/2000 |
| EP | 1 041 933 B1 | 10/2000 |
| EP | 1 050 278 A1 | 11/2000 |
| EP | 1 053 719 A1 | 11/2000 |
| EP | 1 053 720 A1 | 11/2000 |
| EP | 1 055 399 A1 | 11/2000 |
| EP | 1 061 857 B1 | 12/2000 |
| EP | 1 065 981 B1 | 1/2001 |
| EP | 1 079 746 B1 | 3/2001 |
| EP | 1 080 680 A1 | 3/2001 |
| EP | 1 080 694 A1 | 3/2001 |
| EP | 1 082 944 B1 | 3/2001 |
| EP | 1 158 917 B1 | 12/2001 |
| EP | 1 174 093 A1 | 1/2002 |
| EP | 1 179 320 A2 | 2/2002 |
| EP | 1 179 320 A3 | 2/2002 |
| EP | 1 287 788 A1 | 3/2002 |
| EP | 1 205 155 A1 | 5/2002 |
| EP | 1 253 866 B1 | 11/2002 |
| EP | 1 257 220 B1 | 11/2002 |
| EP | 1 330 201 B1 | 7/2003 |
| EP | 1 330 989 B1 | 7/2003 |
| EP | 1 344 498 B1 | 9/2003 |
| EP | 1 374 788 B1 | 1/2004 |
| EP | 1 407 719 A3 | 4/2004 |
| EP | 1 581 128 B1 | 10/2005 |
| EP | 1 599 146 B1 | 11/2005 |
| EP | 1 632 191 A3 | 3/2006 |
| EP | 1 637 087 A3 | 3/2006 |
| EP | 1 693 015 A2 | 8/2006 |
| EP | 1 782 741 A3 | 5/2007 |
| EP | 1 880 686 A2 | 1/2008 |
| JP | 2001-178740 A | 7/2001 |
| WO | WO-96/39914 A1 | 12/1996 |
| WO | WO-97/27893 A1 | 8/1997 |
| WO | WO-97/48346 A1 | 12/1997 |
| WO | WO-98/03117 A1 | 1/1998 |
| WO | WO-98/19625 A2 | 5/1998 |
| WO | WO-98/19625 A3 | 5/1998 |
| WO | WO-98/56324 A1 | 12/1998 |
| WO | WO-99/03407 A1 | 1/1999 |
| WO | WO-99/03408 A1 | 1/1999 |
| WO | WO-99/03409 A1 | 1/1999 |
| WO | WO-99/09919 A1 | 3/1999 |
| WO | WO-99/16359 A1 | 4/1999 |
| WO | WO-99/20213 A1 | 4/1999 |
| WO | WO-99/30655 A1 | 6/1999 |
| WO | WO-99/32042 A1 | 7/1999 |
| WO | WO-99/40858 A1 | 8/1999 |
| WO | WO-99/49799 A1 | 10/1999 |
| WO | WO-00/09053 A1 | 2/2000 |
| WO | WO-00/41638 A1 | 7/2000 |
| WO | WO-00/54683 A1 | 9/2000 |
| WO | WO-00/62685 A1 | 10/2000 |
| WO | WO-00/62698 A1 | 10/2000 |
| WO | WO-00/71043 A1 | 11/2000 |
| WO | WO-01/35845 A1 | 5/2001 |
| WO | WO-01/60273 A1 | 8/2001 |
| WO | WO-01/95819 A1 | 12/2001 |
| WO | WO-02/11635 A1 | 2/2002 |
| WO | WO-02/19932 A1 | 3/2002 |
| WO | WO 03/092521 A1 | 11/2002 |
| WO | WO-02/102255 A1 | 12/2002 |
| WO | WO-03/005882 A2 | 1/2003 |
| WO | WO-03/005882 A3 | 1/2003 |
| WO | WO-03/024305 A2 | 3/2003 |
| WO | WO-03/024305 A3 | 3/2003 |
| WO | WO-03/024339 A1 | 3/2003 |
| WO | WO-03/028542 A2 | 4/2003 |
| WO | WO-03/028542 A3 | 4/2003 |
| WO | WO-03/068311 A2 | 8/2003 |
| WO | WO-03/068311 A3 | 8/2003 |
| WO | WO-03/090638 A1 | 11/2003 |
| WO | WO-2004/002293 A2 | 1/2004 |
| WO | WO-2004/002293 A3 | 1/2004 |
| WO | WO-2004/022155 A2 | 3/2004 |
| WO | WO-2004/022155 A3 | 3/2004 |
| WO | WO-2004/071278 A2 | 8/2004 |
| WO | WO-2004/071278 A3 | 8/2004 |
| WO | WO-2004/073752 A2 | 9/2004 |
| WO | WO-2004/073752 A3 | 9/2004 |
| WO | WO-2004/112581 A2 | 12/2004 |
| WO | WO-2004/112581 A3 | 12/2004 |
| WO | WO-2005/009213 A2 | 2/2005 |
| WO | WO-2005/009213 A3 | 2/2005 |
| WO | WO-2005/072634 A2 | 8/2005 |
| WO | WO-2005/072634 A3 | 8/2005 |
| WO | WO-2005/112806 A2 | 12/2005 |
| WO | WO-2005/112806 A3 | 12/2005 |
| WO | WO-2005/117735 A1 | 12/2005 |
| WO | WO-2005/122936 A1 | 12/2005 |
| WO | WO-2005/122938 A1 | 12/2005 |
| WO | WO-2006/002337 A2 | 1/2006 |
| WO | WO-2006/002337 A3 | 1/2006 |

| | | |
|---|---|---|
| WO | WO-2006/051252 A1 | 5/2006 |
| WO | WO-2006/125007 A2 | 11/2006 |
| WO | WO-2006/125007 A3 | 11/2006 |
| WO | WO-2007/103800 A2 | 9/2007 |
| WO | WO-2007/103800 A3 | 9/2007 |
| WO | WO-2007/143445 A2 | 12/2007 |
| WO | WO-2007/143445 A3 | 12/2007 |
| WO | WO-98/03220 A1 | 1/2008 |

OTHER PUBLICATIONS

Jones, H.M. et al. (1995). "Development of Pulsed Dielectric Breakdown in Liquids," *J. Phys. D: Appl. Phys.* 28:178-188.

Palanker, A.V. et al. (2002). "Effect of the Probe Geometry on Dynamics of Cavitation," *Proc. SPIE* 4617:112-117.

Palanker, D. et al. (Jun. 1, 1997). "Electrical Alternative to Pulsed Fiber-delivered Lasers in Microsurgery," *J. Appl. Phys.* 81(11):7673-7680.

Partial European Search Report mailed on Jul. 3, 2008, for EP Application No. 04 71 1134, filed on Sep. 14, 2005, five pages.

Cushing, H. (Dec. 1928). "Electro-Surgery as an aid to the Removal of Intracranial Tumors," vol. XLVII, No. 6 in *Surgery, Gynecology and Obstetrics*, Martin, F. ed. et al., Chicago, Illinois, U.S.A., pp. 751-784.

European Examination Report mailed on Dec. 12, 2008, for EP Application No. 04755740.0 filed on Jun. 18, 2004, four pages.

European Search Report mailed on Jul. 18, 2007, for EP Application No. 04755740.0 filed on Jun. 18, 2004, four pages.

International Search Report and Written Opinion mailed on May 15, 2008, for PCT Application PCT/US2007/023130, filed on Nov. 1, 2007, eight pages.

International Search Report mailed on Dec. 8, 2005, for PCT Application No. PCT/US04/19785, filed on Jun. 18, 2004, one page.

Mylrea, K.C. et al. (Jul.-Sep. 1981). "Introduction to Electrosurgery," *Journal of Clinical Engineering* 6(3):185-191.

International Preliminary Report on Patentability mailed on Oct. 15, 2009, for PCT Application No. PCT/US2008/004460, filed on Apr. 4, 2008, six pages.

International Preliminary Report on Patentability mailed on May 14, 2009, for PCT Application No. PCT/US2007/023130, filed on Nov. 1, 2007, seven pages.

Miller, J.M. et al. (Jun. 2003). "Precision and Safety of the Pulsed Electron Avalanche Knife in Vitrecoretinal Surgery," *Arch Opthalmol* 121:871-877.

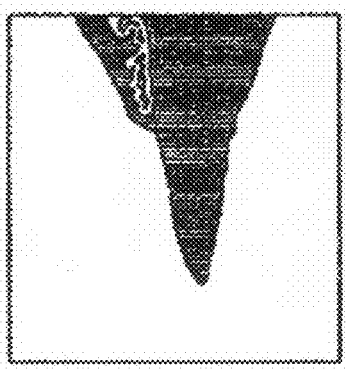
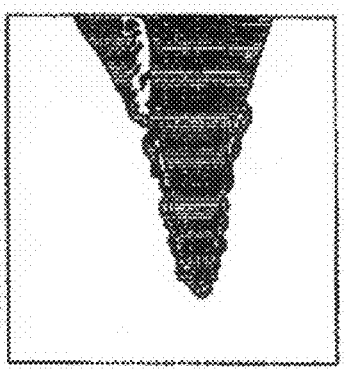
FIG. 5A  FIG. 5B  FIG. 5C
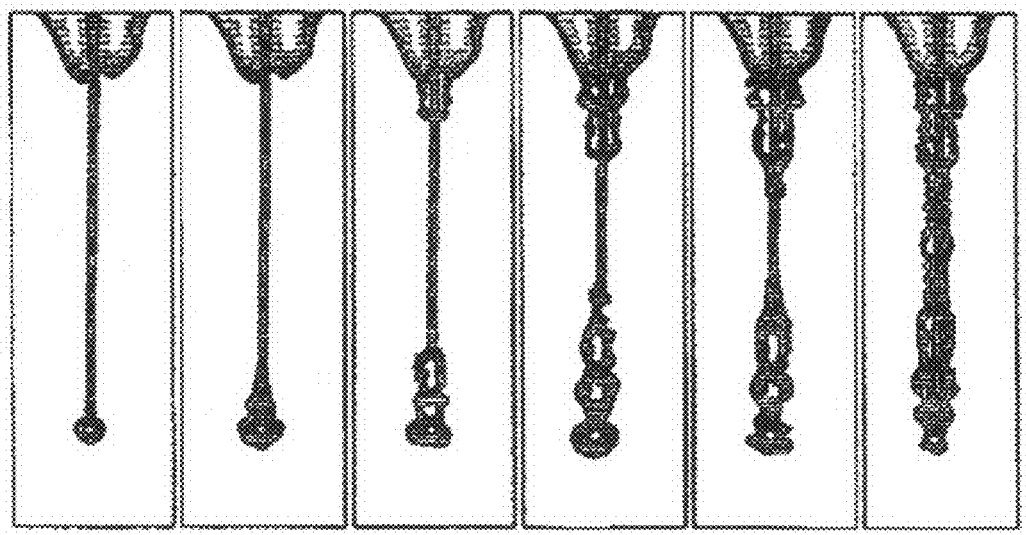
FIG. 6

ELECTROSURGICAL SYSTEM WITH UNIFORMLY ENHANCED ELECTRIC FIELD AND MINIMAL COLLATERAL DAMAGE

STATEMENT REGARDING FEDERALLY SPONSORED RESEARCH OR DEVELOPMENT

This invention was supported by the National Institutes of Health under contract number R01 EY 12888. The government has certain rights in this invention.

FIELD OF THE INVENTION

The present invention relates generally to an electro-surgical device, and in particular, to the design of efficient electrosurgical probes and waveforms for pulsed plasma-mediated cutting, fragmentation, and evaporation of biological tissue in fluid media.

BACKGROUND OF THE INVENTION

Plasma-mediated cutting of biological tissue with sub-microsecond pulses of high voltage is described in the patent of Palanker (U.S. Pat. No. 6,135,998), herein incorporated by reference in its entirety. Dissection of tissue based on explosive vaporization by short (under a few microseconds) pulses of high voltage is described in the patent of Lewis et al. (U.S. Pat. No. 6,352,535). In these applications, an inlaid cylindrical electrode (i.e., a wire embedded into a thick insulator and exposed at its end) is applied to ionize, evaporate and fragment tissue in proximity of the electrode using dielectric breakdown or vaporization of water induced by a high electric field. An inlaid cylindrical electrode cannot penetrate into tissue and thus can only produce shallow cuts on its surface. Due to the pulsed regime of application, this device produces a series of perforations in tissue, which often do not merge into a continuous cut. In addition, cavitation bubbles accompanying each pulse create substantial collateral damage in tissue during their growth and collapse phases. For example, see "Effect of the Probe Geometry on Dynamics of Cavitation," D. Palanker, A. Vankov, and J. Miller, Laser-Tissue Interactions XIII, vol. 4617 SPIE (2002). The size of such a damage zone typically far exceeds the size of the electrode and the corresponding zone of initial energy deposition. Reduction in pulse energy helps to reduce the mechanical damage, but may also lead to decreased cutting depth.

A second mechanism of electrosurgical ablation is formation of plasma following vaporization in the proximity of the probe by either a continuous radio frequency waveform or with sub-millisecond long bursts of pulses. For example, see U.S. Pat. No. 6,780,178, herein incorporated by reference in its entirety. This mechanism is universally applicable to soft and hard biological tissue ranging from membranes and retina to skin and cartilage. In such regimes, wire electrodes are typically used, although the use of a device that could provide a uniform electric field along its length would be preferable.

Without considering end effects, the electric field in a conductive medium at a distance r from a cylindrical electrode with potential U and radius $r_0$ much smaller than its length L is:

$$E = U/(r \ln(r_0/L)) \quad [1]$$

assuming that the return electrode is much larger and positioned at infinity. The threshold electric field required for dielectric breakdown in water is on the order of $10^5$-$10^6$ V/cm (Jones, H. M. & Kunhardt, E. E. Development of Pulsed Dielectric Breakdown In Liquids. Journal of Physics D-Applied Physics 28, 178-188 (1995); Jones, H. M. & Kunhardt, E. E. Pulsed Dielectric Breakdown of Pressurized Water and Salt Solutions. Journal of Applied Physics 77, 795-805 (1995)). Such a threshold electric field $E_{th}$ can be achieved with electric pulses of several kV on a wire electrode with a diameter of several tens of micrometers. The threshold voltage required for ionization of a surface layer of water is:

$$U_{th} = E_{th} r_0 \ln(L/r_0) \quad [2]$$

The corresponding threshold energy is:

$$F_{th} = 2\pi E_{th}^2 r_0^2 L \ln(L/r_0) \quad [3]$$

Evaporation of water in the proximity of an electrode begins when the temperature is elevated above 100° C. The threshold voltage required for vaporization of a surface layer is:

$$U_{th} = (c\rho\Delta T/(\tau\gamma))^{1/2} r_0 \ln(L/r_0) \quad [4]$$

where $\tau$ is a pulse duration, $\gamma$ is the electrical conductivity of the liquid, $\rho$ is the liquid density, c is the liquid heat capacity, and $\Delta T$ is the temperature change. The corresponding threshold energy is:

$$F_{th} = 2\pi c\rho\Delta T r_0^2 L \ln(L/r_0) \quad [5]$$

Lower threshold voltage and energy, as well as better localization of energy deposition can be achieved by decreasing the radius of electrode $r_0$, as follows from equations 1-5. However, this approach is limited by the mechanical strength of the thin wire and its visibility. In addition, the problem of non-uniform distribution of electric field along the electrode, and particularly, enhancement at the apex remains.

This enhancement is illustrated in FIG. 1A, which shows the electric field surrounding a wire electrode. The field is stronger at the apex (i.e., at distance=0) and is weaker in its cylindrical portion. Thus, ionization and vaporization on such an electrode will always begin and be dominant at locations of enhanced field strength, leading to uneven cutting and excessive damage in front of these singular points, as shown in FIG. 2.

One geometry that provides uniform enhancement of an electric field is a ring electrode shown in FIG. 3. Its field is uniform except for the points of deviation from perfectly round shape, such as where the ring electrode contacts with a holder. Fortunately, these regions of deviation can be kept away from tissue during surgery. The threshold voltage on such an electrode is set by the wire radius (e.g., see equations 2 and 4) and thus may be limited by the mechanical strength of the wire. For example, a thin wire is very weak and flexible and is thus inapplicable to manipulation of tissue. In addition, wires thinner than 25 microns are barely seen under a conventional surgical microscope, and this makes their use even more difficult. An additional problem with the application of thin wires is that erosion of thin wires greatly limits their lifetime.

Erosion of the blade may occur because of electrochemical or thermal reactions on the electrode, and may be a problem for existing electrosurgical electrodes, including electrosurgical blades. Such blades typically have flat sides and an exposed active edge. During electrosurgical cutting with plasma, the plasma formed along the exposed electrode surface may result in localized high temperatures that may differentially etch the electrode and the adjacent insulation. The result is to change the geometry of the cutting electrode, which may be particularly undesirable, and may affect the ability to cut with the electrode, as well as the energy required to drive the electrode.

For example, FIGS. 10A to 10C illustrate differential erosion of electrodes. FIG. 10A shows an initial cross-section through a cutting electrode. The conductive metal region of the electrode 1001 is surrounded by insulation 1003, except at the exposed tip 1005. When this electrode is to be used with electrosurgical (plasma) cutting, appropriate electrical stimulation may be applied to the electrode so that plasma is formed at the tip 1007. If the vaporization or melting temperature of the insulation 1003 is less than the temperature reached by the plasma (e.g., approximately 800° C.), the insulation may be removed from the electrode, as shown in FIG. 10B. In FIG. 10B, the insulator has retreated from the cutting region of the electrode during activation of the plasma (e.g., plasma-mediated electrosurgery), exposing the conductive metal 1001, which may lead to an increase in electric current flowing from the electrode into the conductive medium or tissue. This results in higher power dissipation which may lead to increase generation of heat in the tissue volume, formation of excess gas (bubbles), an increase in the zone of electroporation damage, and unstable generation of plasma during surgery. This problem may be a result of insulation materials having a low-melting and/or vaporization point (e.g., volatile insulators such as plastics). Such materials may vaporize or erode faster than the metal electrode during a plasma mediated electrosurgical application, as shown. However, a parallel problem may result when the insulation layer is too resistant to erosion, as shown in FIG. 10C. In this example, the insulation does not erode as rapidly as the metal electrode erodes. As the conductive metal erodes from the insulation, a gap is formed between the metal, resulting in a gap between the conductive metal and the surrounding material. At some point this gap may prevent cutting of tissue by the electrode, either because of physical separation from the tissue, or because the voltage will be insufficient for vaporization and ionization, terminating the electric discharge.

Below we describe probe geometry and pulse waveform structures that provide solutions to these and other problems.

BRIEF SUMMARY OF THE INVENTION

Described herein are cutting electrodes that can cut tissue uniformly along an extensive cutting zone, rather than just with its apex (e.g., tip). Such electrodes may be referred to as blade electrodes, or blade cutting electrodes. As will be shown below, this objective can be achieved through geometric tailoring of the electrode, which may be matched to the electrical stimulation applied to the electrode. In particular, we describe electrodes having a thin narrow exposed cutting surface that is surrounded by an insulation layer that is matched to the geometry of the exposed electrode region.

Tissue can be cut uniformly along an extensive cutting zone through the use of an electrosurgical cutting system that comprises an electrically conductive blade, insulators, and a source of pulsed electrical energy coupled to the blade. In particular, the blade may have a first blade surface, a second blade surface, and a blade thickness. The blade thickness is the smallest local distance between the first blade surface and the second blade surface. First and second insulators may be affixed to the first and second blade surfaces, respectively. The first blade surface and the second blade surface come together along a blade edge. In some variations, the blade edge is perfectly sharp, but may be somewhat rounded. The rounded region between the first and second blade surfaces may also be called the blade edge. The blade edge may have an edge radius of curvature, which can be small (thereby providing a sharp blade edge). In some instances, a portion of the blade edge instead of the entire blade edge may be used for cutting. This blade cutting portion may be a predetermined length of the blade that is used for cutting biological tissue. Unlike the ring electrode discussed earlier, the use of a blade may provide substantial mechanical strength while the use of a blade edge with a small edge radius of curvature can provide a substantially uniform enhanced electric field along its cutting zone.

In some variations, biological tissue is cut with the electrosurgical system with a sharp blade edge by manipulating the blade such that the sharp blade edge is in close proximity to the tissue to be cut. The approach then involves applying at least one electrical pulse along the cutting zone of the blade edge that contacts the region of biological tissue to be cut. In one variation, multiple electrical pulses are applied to the sharp blade edge. The electrical pulses may be of sufficient strength to generate electric breakdown in the tissue that is in a close proximity to the sharp blade edge. The pulse duration may be sufficiently long for the generation of a streamer and spark discharge but sufficiently short to avoid the development of a high current arc discharge. In this case, whether the current was high would be with comparison to the current generated in the biological medium prior to the development of the arc.

Tissue can also be cut uniformly along an extensive cutting zone without the use of a blade as described above. In this approach, biological tissue immersed in a liquid medium can be cut uniformly along a cutting zone of an electrode (not necessarily in the form of a blade) by first forming a uniform vapor cavity surrounding the cutting zone of the electrode. This can be accomplished through the tailoring of the electrical pulses applied to the electrode. After forming the uniform vapor cavity, this approach involves ionizing the vapor in the cavity. This results in a plasma-mediated discharge into the biological tissue inside the vapor cavity.

These two approaches can be combined to form very effective methods for cutting biological tissue. In the combined approach for cutting biological tissue, a burst of pulsed electrical energy is applied to a blade having a blade edge with a relatively small edge radius of curvature. The number of pulses and the energy of each pulse is chosen such that, at some time prior to completion of the burst of pulses, vaporization occurs along the entire blade cutting portion of the blade edge. With the combined approach, nonuniformities in the electric field along the blade edge are effectively smoothed out.

In some variations of the methods described herein, the electrical pulses are bipolar. In other variations, the electrical pulses are monopolar. In yet further variations, the electrical pulses may have alternating polarity. Alternating the polarity of the pulses may greatly reduce the electroporation-related tissue damage away from the immediate vicinity of the cut.

An electrosurgical cutting system as described herein can be readily fabricated. A blade of an electrically conductive material may be provided. The blade may have a first blade surface and an opposing second blade surface. The first and second blade surfaces join at a blade edge. In some variations, the first and second blade surfaces in a predetermined cutting zone near the blade edge are tapered to form a tapering region, which is the region in which the first and second blade surfaces converge towards each other. The blade may be coated with a thin layer of insulator to form a coated blade. The coated blade may then be immersed in a conductive medium, and a source of pulsed electrical energy coupled to the blade. Pulsed electrical energy is then applied to the blade until the thin layer of insulator is removed from the vicinity of the blade edge. The thin layer of insulator may be removed over the entire edge (which in some variations may include the entire tapering region).

Also described herein are electrosurgical blades for use with an electrosurgical power supply. In some variations, these blades include an electrode having an insulated area and an exposed edge region having an exposed edge thickness of between about 1 µm and about 100 µm, and a glass enamel insulator layer extending at least partially along the length of the electrode. The insulator layer abuts the exposed electrode edge region and surrounds the exposed electrode edge region, and the insulator layer has a thickness between about half to about three times the thickness of the exposed electrode edge region.

The electrode of the electrosurgical blade may be made of a metal selected from the group consisting of titanium, tantalum, molybdenum, tungsten and stainless steel. In some variations, the electrode is formed from a metal foil having a thickness of between about 10 µm to about 50 µm. The glass enamel insulator may be made of a high temperature grade, lead-free enamel. In some variations, the insulated length of the blade is greater than about 0.1 mm.

The blade, and particularly the edge of the blade, may be any appropriate shape or curvature. For example, the electrosurgical blade may have a length of the exposed active electrode edge region that is substantially straight, or curved, or a combination of straight and curved regions. In some variations, the electrosurgical blade forms a scoop where the exposed edge region is disposed along the perimeter of the scoop. In some variations, the shape of the exposed edge region of the electrode includes a region that is selected from the group consisting of: L-shape, U-Shape, V-shape, O-shape, or a combination of these shapes. In general, the exposed edge region of any of the electrode blades (or cutting electrodes) described herein may be configured to form a substantially uniform electrical field when power is supplied by the electrosurgical power supply. For example, the exposed region of the electrode blade (the edge region) may be of relatively uniform cross-section along its length, and/or may be of relatively similar distance from an electrical return pathway.

Any of the electrodes described herein may include a handle interface that is configured to secure the electrosurgical blade to a handle so that the electrode may make electrical contact with the electrosurgical power supply. Thus, blades may be inserted into a re-usable handle.

Also described herein are electrosurgical blades for use with an electrosurgical power supply that have a planar electrode with an upper insulated surface and a lower insulated surface, and an exposed edge region, and a first insulation layer covering the upper surface, and a second insulation layer covering the lower surface, wherein the thickness of the first and second insulation layers are between about 0.5 and 3 times the electrode thickness therebetween. The upper and lower insulated surfaces may extend from the exposed edge region by a length that is greater than about 100 µm, and wherein the upper and lower surfaces are separated from each other by an electrode thickness between about 10 µm and 100 µm over this length. Thus, the electrode may have a region near the edge that is relatively flat before reaching the un-insulated edge. This region may allow the blade to be used so for an extended period of time as long as there is relatively uniform erosion of the conductive metal blade and the overlaying insulation.

In some variations, the planar electrode portion (the conductive metal portion of the electrode) is formed from a conductive metal foil that is selected from the group consisting of titanium, tantalum, molybdenum, tungsten and stainless steel foils.

The first and second insulation layers may comprise a material having a softening point or melting point between about 400° C. and 900° C. The softening or melting point of the insulation may be adjusted (particularly within this range) so that during plasma formation, the rate of erosion of the metal matches the rate of erosion of the insulation, particularly at the thicknesses of metal and insulation specified. In some variations, the first and second insulation layers comprise glass enamel. Other insulation materials for the first and second insulation layers include glass, ceramics, and plastics.

Also described herein are electrosurgical blades for use with an electrosurgical power supply that include an active electrode having an insulated length and an exposed edge region (the exposed edge region having an exposed edge thickness of between about 1 µm and about 100 µm), and an insulator layer extending at least partially along the length of the active electrode, where the insulator layer abuts the exposed electrode edge region and surrounds the exposed electrode edge region. The insulator layer has a thickness between about half to about three times the thickness of the exposed electrode edge region, and at least a portion of the exposed edge and the surrounding insulator layer form an edge profile. In this variation, the insulator layer and the active electrode edge region may erode at approximately the same rate when the electrosurgical blade is activated by the electrosurgical power supply, substantially preserving the edge profile as the active electrode edge region and insulator layer are eroded.

As described above, the insulator layer may be made of any appropriate material, particularly glass (e.g., lead-free enamel). The active electrode may be formed of a metal foil, (e.g., titanium, tantalum, molybdenum, tungsten, gold, stainless steel, etc.). The foil may be any appropriate thickness. For example, the electrode may be formed from titanium foil that is approximately 15 µm thick.

The electrosurgical blades (blade electrodes) described herein may be any appropriate length. For example, the length may be between about 0.1 mm and 15 mm. Specifically, the electrosurgical blade length may be greater than about 0.1 mm, greater than about 0.2 mm, greater than about 0.5 mm, between about 0.1 mm and 5 mm, or any intermediate size. As described above, any of the electrosurgical blades described herein may have an exposed edge region that is substantially straight, curved, or some combination thereof, including being formed in a substantially L-shape, U-Shape, V-shape, O-shape, or a combination of these shapes.

Also described herein are methods of fabricating an electrosurgical blade. In some variations, the method includes the steps of applying a thin coating of insulator to an electrode having an elongated edge region so that the edge region is covered by the insulator, and removing the insulator from the edge region by applying electrical energy to the electrode to expose the elongated edge of the electrode.

In some variations, the step of applying a thin coating of insulator to an electrode may include applying a thin coating of insulator to a metal foil, and/or applying a thin coating of insulator to an electrode having an elongated edge with a thickness between about 1 µm and about 100 µm. In some variations, the step of applying a thin coating of insulator to an electrode involves applying a thin coating of insulator to an electrode made of a metal selected from the group consisting of titanium, tantalum, molybdenum, tungsten, gold and stainless steel.

When applying the coating of insulator to the electrode, the insulator may be applied to a thickness of between about half to about three times the thickness of the edge region of the electrode. Thus, the insulation may be applied by spraying the electrode with an insulating material. The application of the insulation material may involve the application of a material that will become the insulation layer. For example, the application of insulation material may involve the application of a solution or suspension that sets, dries, and/or cures into the insulation material. Thus, the thickness and amount of insulation applied may appear thicker (e.g., because of water content, etc.) but when cured it will assume the thickness referred to by "thickness of between about half to about three times the thickness of the edge region." In some variations, the step of applying a thin coating of insulator to an electrode comprises dipping the edge region of the electrode into an insulating material in order to form the coating.

As mentioned briefly, the step of applying a thin coating of insulator to an electrode may also include curing the insulator onto the electrode, including heat-curing. For example, when the thin coating of insulator to an electrode comprises applying a glass enamel to the electrode, the glass enamel may be applied "wet" and later be cured onto the electrode (including the blade and edge region) to assume the appropriate thickness.

The method of fabricating the blade electrode may also include a step of removing the insulation over the edge (the cutting region) of the blade electrode. This may be done by any appropriate method, including grinding. In particular, the method may include electrically connecting the electrode to a source of electrical energy, and then removing the insulator from the edge region by applying electrical energy to the electrode by applying pulsed RF energy to the electrode. In some variations, removing the insulator from the edge region by applying electrical energy to the electrode comprises forming a plasma discharge at the elongated edge region of the electrode. The electrode may be immersed in conductive liquid medium when this is performed.

Also described herein are methods of fabricating an electrosurgical blade including the steps of providing an electrode having an edge region sufficient to focus an applied electrical field, (wherein the edge region has a thickness of less than about 200 µm), applying a thin coating of insulator to electrode including the edge region, and removing insulator from the edge region by applying pulsed electrical energy to the electrode to form an electrical discharge at the edge region of the electrode. Thus, the electrode may be connected to a source of electrical power. The "electrode" referred to herein includes the conductive metal that will form the edge (the cutting or active region). It is understood that the electrode may include additional regions (including a sheath or support region) that may also be conductive, but that does not typically include the exposed cutting region.

In some variations, the step of providing an electrode includes providing an electrode having an edge region with a thickness of less than 100 µm. The edge region of the electrode may be formed of metal foil. In some variations, the insulator applied may be a thin coating of an insulator having a softening point or melting point below 800° C. In some variations, the step of applying a thin coating of insulator comprises applying a thin coating of a glass epoxy insulator.

As described above, the step of removing insulator from the edge region may include applying pulsed electrical energy to form a plasma discharge.

Also described herein are methods of fabricating an electrosurgical blade that include the steps of providing an electrode having edge region that is less than about 200 µm thick, applying a thin coating of glass to the edge region, and removing the glass insulation from the edge region of the electrode by applying electrical energy to the electrode.

BRIEF DESCRIPTION OF THE DRAWINGS

FIG. 5A shows a blade electrode with insulated flat sides and an exposed sharp edge and tapering region on a perimeter. FIG. 5B shows light emission by plasma forming on the exposed portion after a 200 ns pulse of 3.4 kV in saline. FIG. 5C shows vapor (cavitation) bubbles uniformly covering the exposed portion 5 µs after the pulse.

FIG. 6 shows a sequence of photographs demonstrating formation of a uniform cavity along an electrode with a non-uniform electric field using a sequence (burst) of pulses. For complete coverage of the electrode the duration of the burst should not exceed the lifetime of the first bubble.

FIG. 8A shows the electrode before the vapor cavity formation. FIG. 8B shows a vapor cavity forming over the portion of the electrode not covered by the insulator. When the electrical potential is high enough, an electric discharge occurs between the electrode and the tissue as shown in FIG. 8C. As shown in FIG. 8C, the discharge is concentrated in the region of smallest separation (least resistance) between the electrode and the tissue. FIG. 8D is similar to FIG. 8C with a different electrode configuration.

DETAILED DESCRIPTION OF THE INVENTION

Figure 4A:
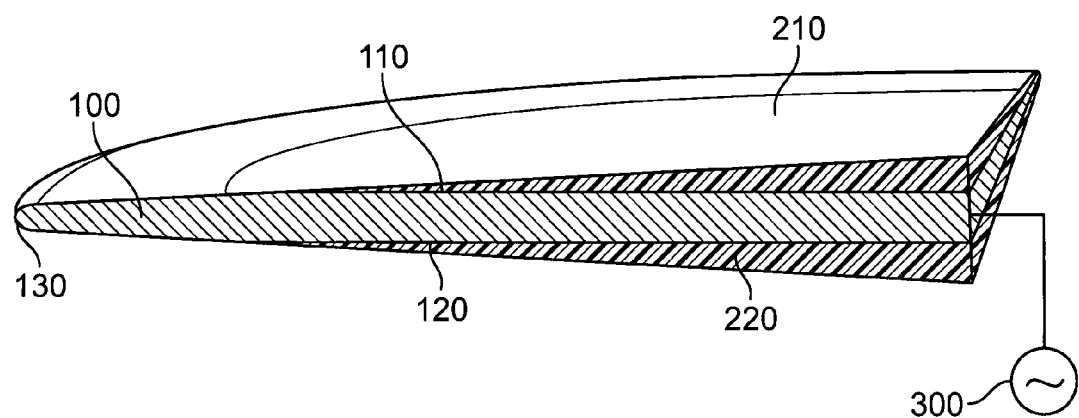
FIG. 4A shows an electrically conductive blade with insulators adjacent to the blade surfaces. The blade surfaces join at a blade edge.

Referring now to the drawings, where similar elements are numbered the same, FIG. 4A depicts an electrically conductive blade 100 having a first blade surface 110, a second blade surface 120, and a blade edge 130. In practice, the blade edge 130 is somewhat rounded, the edge radius of curvature 140 being shown in the magnified view of FIG. 4B. A first insulator 210 is affixed to the first blade surface 110. Similarly, a second insulator 220 is affixed to the second blade surface 120. To complete an electrosurgical cutting system, a source of pulsed electrical energy 300 is coupled to the blade 100. The other terminal from the source of pulsed electrical energy 300 is connected to a return electrode (not shown) immersed in the medium in which the blade 100 is inserted.

At any position on the blade 100, the blade thickness is the smallest distance between the first blade surface 110 and the second blade surface 120. In some embodiments, in the region adjacent the blade edge 130, the blade thickness is reduced approximately linearly as the first 110 and second 120 blade surfaces approach the blade edge 130. A blade tapering angle 150 is the angle of convergence of the first 110 and second 120 blade surfaces as the blade edge 130 is approached. In some embodiments the blade tapering angle 150 is less than 45 degrees; in other embodiments the blade tapering angle 150 is less than 30 degrees; and in the still other embodiments the blade tapering angle 150 is less than 15 degrees. The blade may include an adjacent, auxiliary edge region that is immediately behind the cutting edge of the electrode, which may not be tapered, or may be only slightly tapered. This region is typically insulated, and may form a 'new' blade edge as the exposed edge (and any adjacent insulation) is eroded. This is described in greater detail below.

Figure 4B:
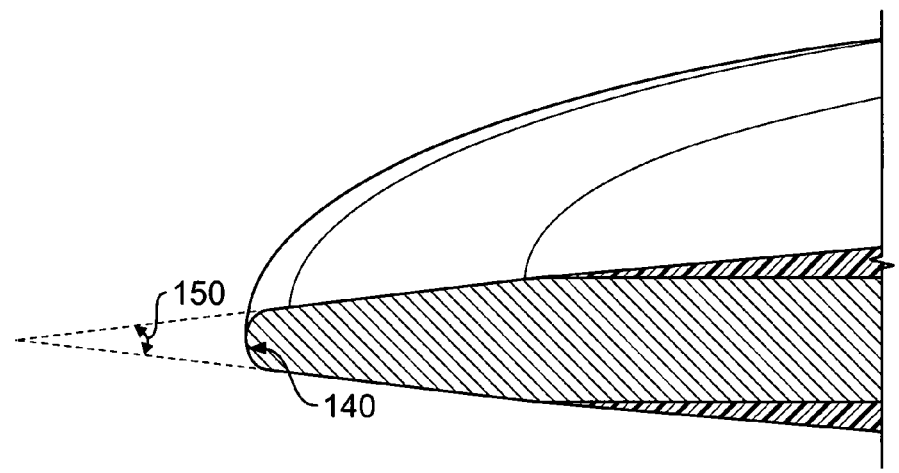
FIG. 4B shows a magnified view of the region around the blade edge. The blade tapering angle and the edge radius of curvature are shown.

In some embodiments the first 210 and second 220 insulators extend completely to the blade edge 130. In some embodiments the first 210 and second 220 insulators terminate prior to the blade edge 130, leaving an exposed portion of the blade 100. In FIGS. 4A and 4B, the exposed portion of the blade 100 extends through all or most of the tapering region. The exposed portion of the blade 100 between the blade edge 130 and the first 210 and second 220 insulators may not significantly reduce the electric field on the blade edge 130, but it may decrease electrical impedance, and increases the energy deposited into the biological tissue. Ending the first 210 and second 220 insulators some distance from the blade edge 130 keeps the insulators away from stresses induced by pulsed heating, vaporization and ionization. The extra distance also provides for some depth of metal for etching, which helps to increase the productive lifetime of the blade 100.

Figure 4C:
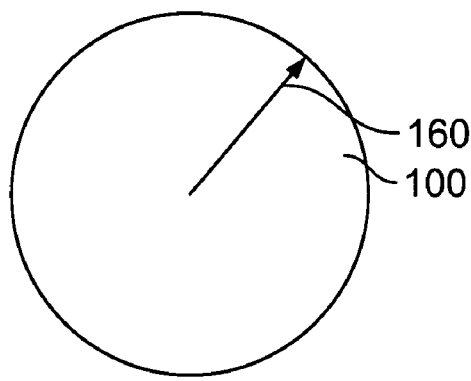
FIG. 4C shows a blade having a circular planform.
Figure 4D:
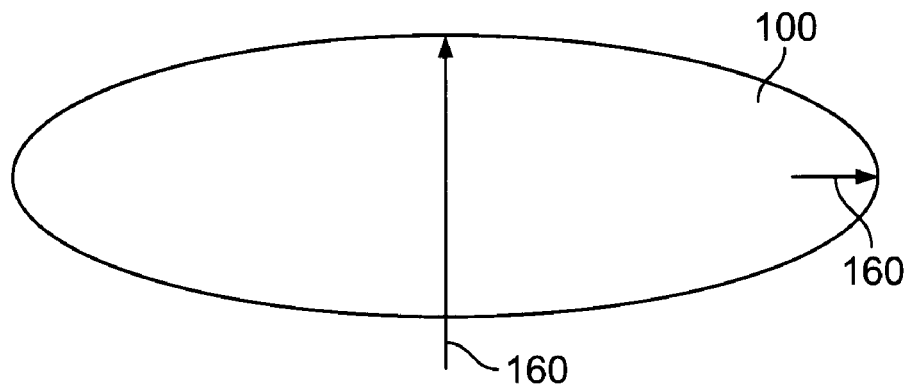
FIG. 4D shows a blade with an elliptical planform.
Figure 4E:
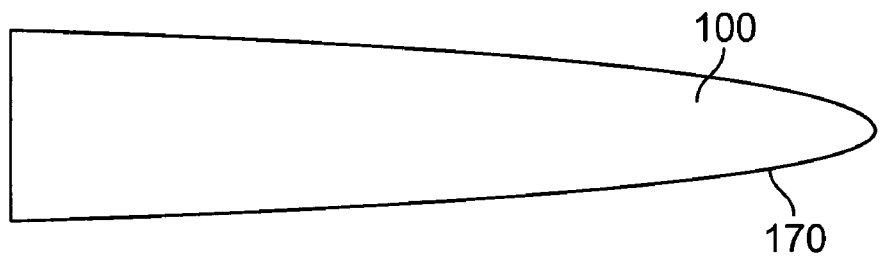
FIG. 4E shows a blade having a planform of more general shape, with the heavier line weight corresponding to the blade cutting portion.

FIGS. 4C-4E show a variety of planform, or in-plane, shapes that may be useful in various embodiments of the blade 100. In a canonical embodiment shown in FIG. 4C, the blade 100 takes the form of a disk, and hence the blade 100 is sometimes denoted a disk electrode. In such a blade 100, the first and second blade surfaces each has a radius of curvature in a plane perpendicular to the thickness, (sometimes known as the planar or in-plane radius of curvature 160) that is constant at all points on the blade 100. In another canonical embodiment shown in FIG. 4D, the blade 100 has an elliptical planform and the planar radius of curvature 160 (shown only schematically) varies considerably along the blade edge.

The planform shown in FIG. 4E is more general. In preferred embodiments the planar radius of curvature 160 is much larger than the edge radius of curvature, at least in the blade cutting portion 170. The blade cutting portion 170 is a predetermined length of the blade 100 that is used for cutting biological tissue. The width of the blade 100 in FIG. 4E may be the thickness of the metal blade region. In FIG. 4E, the blade cutting portion 170 coincides with the heavier line. In some variations, the planar radius of curvature 160 in the blade cutting portion 170 is at least 5, 10, 25, 50, 100, or even thousands of times greater than the edge radius of curvature. Regions where the planar radius of curvature 160 is much greater than the edge radius of curvature are considered to have a sharp blade edge. Having an extensive blade cutting portion 170 with a sharp blade edge may facilitate uniform (or nearly uniform) enhancement of the electric field along the blade edge of the blade cutting portion 170. In some variations, the exposed (e.g., uninsulated) portion of the blade cutting portion 170 is only the very edge of the conductive metal blade.

Electrode with Uniformly Enhanced Field for Dielectric Breakdown

Figure 1A:
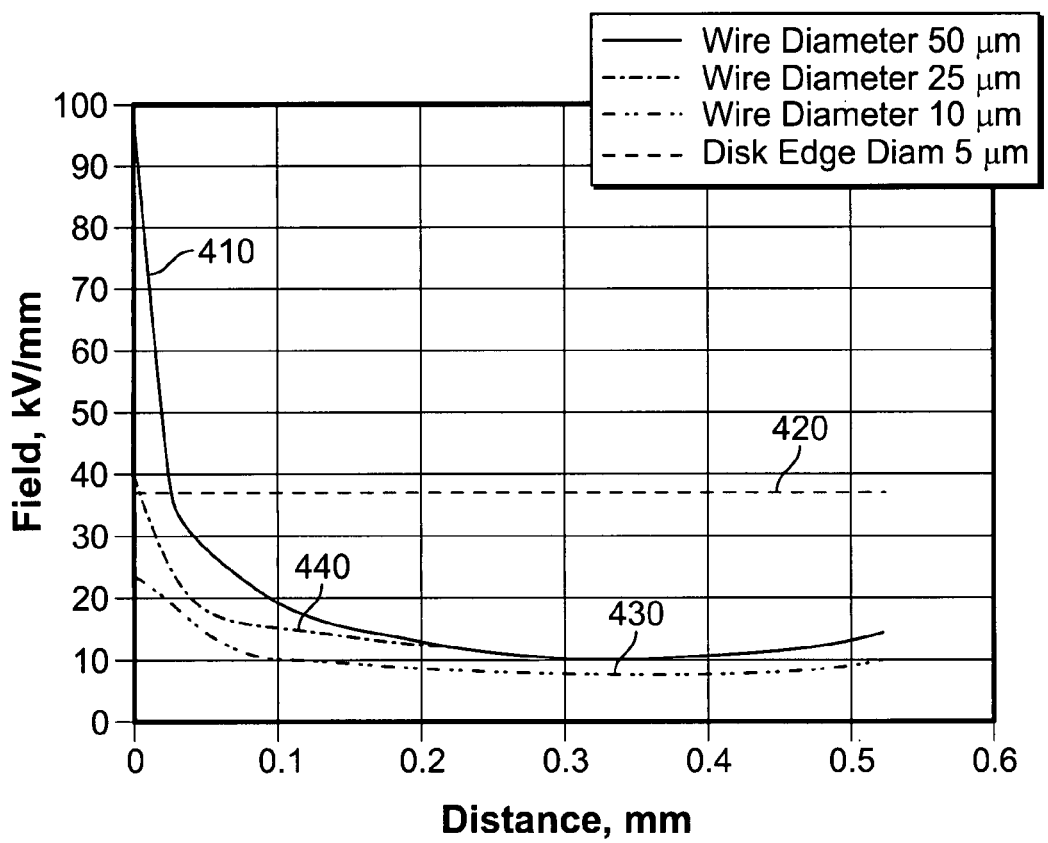
FIG. 1A illustrates the electric field along wire electrodes of 10, 25 and 50 microns in diameter (410, 440, and 430 respectively) and 530 microns in length, and along the 5 µm-thick edge of a disk electrode of 400 µm in diameter (420). The exposed zone of the disk electrode is 50 µm from the edge. The electrode potential is 600 V in all cases.
Figure 1B:
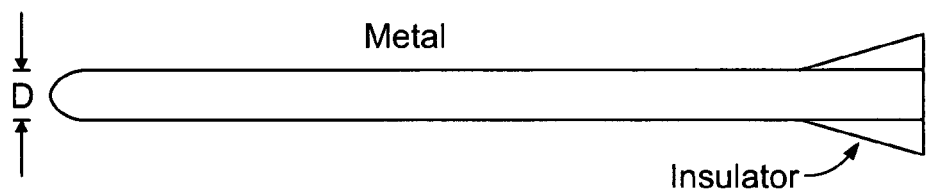
FIG. 1B illustrates the edge of the disk electrode used in FIG. 1A.
Figure 2:
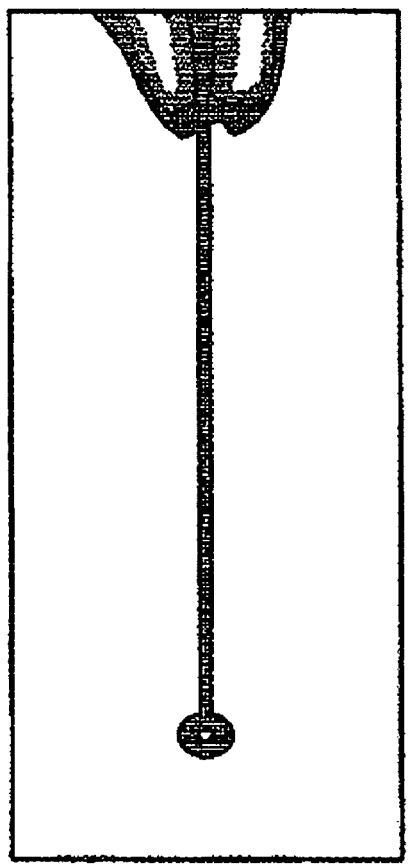
FIG. 2 shows the formation of a cavitation (vapor) cavity at the apex of the wire electrode in saline several microseconds after beginning of electrical pulse. This effect demonstrates that electric field at the apex is much higher than in other parts of the wire electrode.
Figure 3:
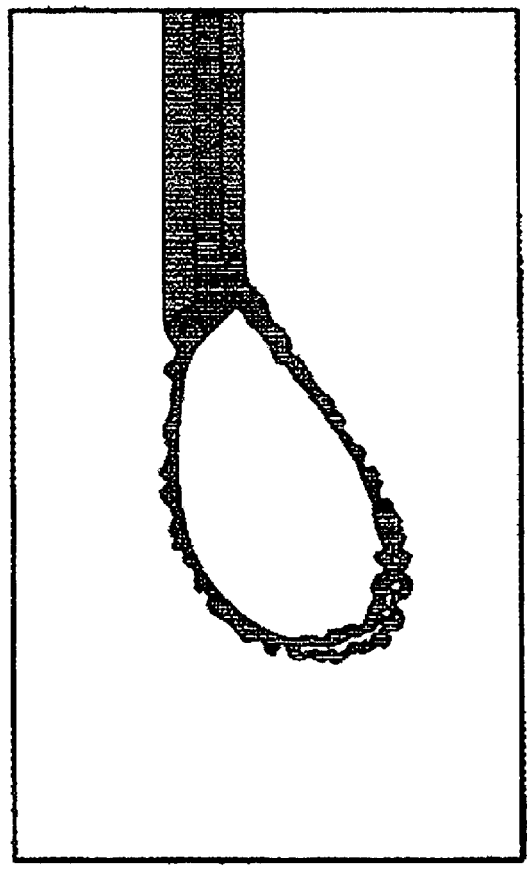
FIG. 3 shows a 10 µm-thick wire loop electrode in saline with cavitation bubbles forming simultaneously along all its length. This effect demonstrates the uniformity in distribution of the electric field along its surface.

The electric field around a sharp exposed blade edge is similar to that on a ring electrode, but the radius of curvature is not as limited in mechanical strength. The blade edge can be sharpened because the mechanical strength for this structure is provided by the blade. In addition, visibility of blade electrodes is not a problem as compared to thin wire electrodes, since the macroscopic blade can be easily observed while its blade edge might not be well resolved in a conventional surgical microscope. Thus, the blade edge of such an electrode can be sharp (e.g., have an edge radius of curvature much smaller than 10 microns and still be visible. This may strongly reduce the threshold voltage and energy, as well as the penetration depth of the field into the tissue, which in turn leads to a cleaner cut with a smaller zone of damaged tissue. The distribution of electric field along a 5 µm-thick blade edge on a disk electrode is shown in FIG. 1. Blades that have a thin edge (e.g., less than about 100 µm, less than about 50 µm, less than about 20 µm, less than about 15 µm, etc.) may also be considered "sharp", regardless of the edge radius of curvature, similar to the thin wire electrodes described above.

The small radius of curvature and low threshold energy may make the interaction zone with tissue very shallow, and thus fast cutting can be achieved at sufficiently high pulse repetition rates. Cutting tissue by small steps at high repetition rate may result in a very smooth action leaving very clean edges of the lesion. The layer of insulator on the flat sides (first and second blade surfaces) may be thin—comparable or thinner than the edge radius of curvature. This may help with insertion into the tissue, and may also help with erosion and formation of plasma, as described in more detail below.

If the blade edge is sharp with nearly uniform edge radius of curvature, the electric field on the blade edge may remain uniform, or nearly uniform, even if the planar shape of the electrode is not exactly round. The electric field may remain uniform as long as the planar radius of curvature of the blade remains much larger than the edge radius of curvature of the blade edge and the edge radius of curvature is uniform or nearly so. Thus, a disk electrode can be deformed into an ellipse or other blade shape. Such a blade electrode will preserve a substantially uniform distribution of electric field along the blade edge and can be used for uniform dissection or ablation of tissue with any part on its perimeter. Examples of uniform formation of vapor bubbles and ionization along the blade edge of such an electrode are shown in FIGS. 5A-5C.

Tapering Angle and Material for the Blade Electrode

In variations where the region adjacent to the edge of the electrode is not insulated, the field enhancement at the blade edge of the blade electrode may depend on the blade tapering angle. In some variations, a lower the tapering angle means a greater enhancement of the electric field. In addition, a lower blade tapering angle may facilitate access and penetration into the tissue. The threshold energy may be reduced by a factor of 2 when the tapering angle changes from 30° to 0°. Thus, the blade tapering angle may be less than 45°, less than 30°, and less than 15°.

To reduce the rate of etching of the blade by hot plasma, the blade electrode should be made of a material capable of withstanding high temperatures. In addition, the material should be hard enough to provide sufficient rigidity when used as a thin blade. Additionally, to reduce the outflow of heat from the treated area via the blade electrode, it should be made of a material with low thermal conductivity. Materials fitting all these characteristics are for example, Tungsten, and more preferably titanium since its thermal conductivity is 8 times lower.

Pulse Structure

One of the mechanisms of undesirable tissue damage in electrosurgery is electroporation. This may be a direct effect of high electric fields on the membranes of cells. Electroporation typically results in an increase of the cell permeability and may lead to cell injury or death. To reduce this effect a voltage-balanced or a charge-balanced pair of pulses of opposite polarity instead of a single pulse of one polarity can be applied. This change leads to significant reduction in tissue damage. For example, application of a single pulse of 200 ns duration and 4 kV in amplitude produces electroporation-related damage on the order of 260 µm, while charge-balanced bi-phasic pulses applied to the same electrode at the same amplitude produces only 90 µm of electroporation-related damage (measured on chorioallantoic membrane of chicken embryo using Propidium Iodide staining technique). In addition to its biological advantage, alternating the polarity of the pulses may also decrease the erosion rate of the electrode.

In some variations, a microblade of 0.2-0.6 mm in length with insulated flat sides and exposed sharp edges serves as an electrode using bi-phasic charge-balanced waveforms with pulse duration varying from 0.1 to 5 µs. Retinal dissection has been performed with complete and partial vitrectomy on excised pig eyes and in-vivo rabbit eyes. Results were analyzed clinically and histologically. When no energy is applied the instrument can be used as a vitreoretinal pick to elevate and expose membranes. A train of charge-balanced pulses of alternating polarity can create uniform cutting along the edge of the blade without generation of visible gas in vitreous or fluid medium. Smooth cutting without turbulent flow or other mechanical interference occurs when operating at repetition rates around 100 Hz. Histology and propidium iodide staining of live tissue demonstrate that the collateral damage zone extends 40-80 µm from the edge. With different waveforms the blade electrode can also coagulate.

Thus, in some variations electroporation may be reduced by applying a symmetric AC waveform, (voltage-balanced rather that charge-balanced), which may result in a damage zone less than 40 µm.

Pulsed Waveform for Neutralization of "Hot Spots"

Uneven distribution of the electric field along an electrode may affect its performance not only in the regime of dielectric breakdown in liquid, but also in the regime of evaporation of water. This effect can be neutralized using specially designed pulse waveforms. The energy should be delivered in a burst of pulses in such a way that evaporation of the liquid, leading to vapor bubble growth, first occurs in the areas of high electric field. Providing that the electric field is not sufficiently strong for ionization inside the vapor bubble, the vapor bubble may isolate that part of electrode from the conductive fluid. Hence, evaporation will begin in the surrounding areas having a somewhat weaker electric field. This process may continue until the last area of the electrode is covered by the vapor cavity before the first bubble collapses exposing the electrode in that area. This requirement sets the amplitude and optimal duration of the pulse or burst of pulses. The size of individual bubbles and the number of them can be set by choosing the energy of each pulse in the burst and by number of pulses. An example of such process producing uniform vapor cavity along an electrode with a non-uniform electric field is shown in the sequence of photos of FIG. 6. Although the examples herein describe the use of the cutting electrode primarily in a liquid medium (e.g., a conductive liquid medium), these cutting electrodes may be used without being submerged or surrounded in a conductive liquid medium. For example, these electrodes may be used "dry", and the fluid that is vaporized and/or ionized in forming the plasma may come from the material being cut (e.g., tissue).

In the example of FIG. 6, the wire diameter is 25 microns and the wire length is 1 mm. A single burst of pulses is applied to the wire, having a burst duration of 30 µs, and containing pulses (or minipulses) having a duration of 2.5 µs separated by a pulse interval of 2.5 µs. The pulse voltage is 360 V.

The lifetime of an empty spherical cavity of radius $R_0$ in water (density $p=1000$ kg/m$^3$) and under atmospheric pressure ($P_0=10^5$ N/m$^2$) is $t=0.91\ R_0(\rho/P_0)^{1/2}$. That means an empty bubble with radius 100 µm will collapse in approximately 10 µs. If the bubble is not empty, i.e., if the vapor pressure inside is significant, the lifetime will increase. No simple estimates for the cavity lifetime is known, but as a first approximation P, which is a difference between the pressure outside and inside the bubble, can replace $P_0$. Thus, if the vapor pressure inside is $0.9\ P_0$, then $P=0.1\ P_0$, and the lifetime t will increase by a factor of $10^{1/2}$, approximately 3. As the vapor pressure inside the cavity approaches atmospheric pressure the lifetime of the bubble extends to infinity. The amount of vapor inside the cavity depends on the dynamics of the cavity formation. If the bubble is formed as a result of a very fast (as compared to lifetime of the cavitation bubble, which is typically above 10 microseconds) explosion the cavity quickly becomes very cold and is virtually empty. If the bubble is formed by slow (above 10 microseconds) heating and vaporization, the vapor pressure inside will be higher and closer to ambient pressure. These theoretical guidelines can be used to help design waveforms, but some experimentation is likely to be necessary to determine the best waveforms for any particular set of circumstances.

The duration of a burst of pulses is preferably less than 10 ms, and can be less than 1 ms or even less than 0.1 ms, to reduce thermal damage to tissue being cut. The duration of pulses within a burst is preferably between 10 ns and 10 µs.

Preferably, adjacent pulses within a burst of pulses have opposite polarity to reduce electroporation damage to tissue. Bursts may be repetitively applied to the electrode such that successive bursts are separated by a burst interval of 1 ms or more.

Figure 7A:
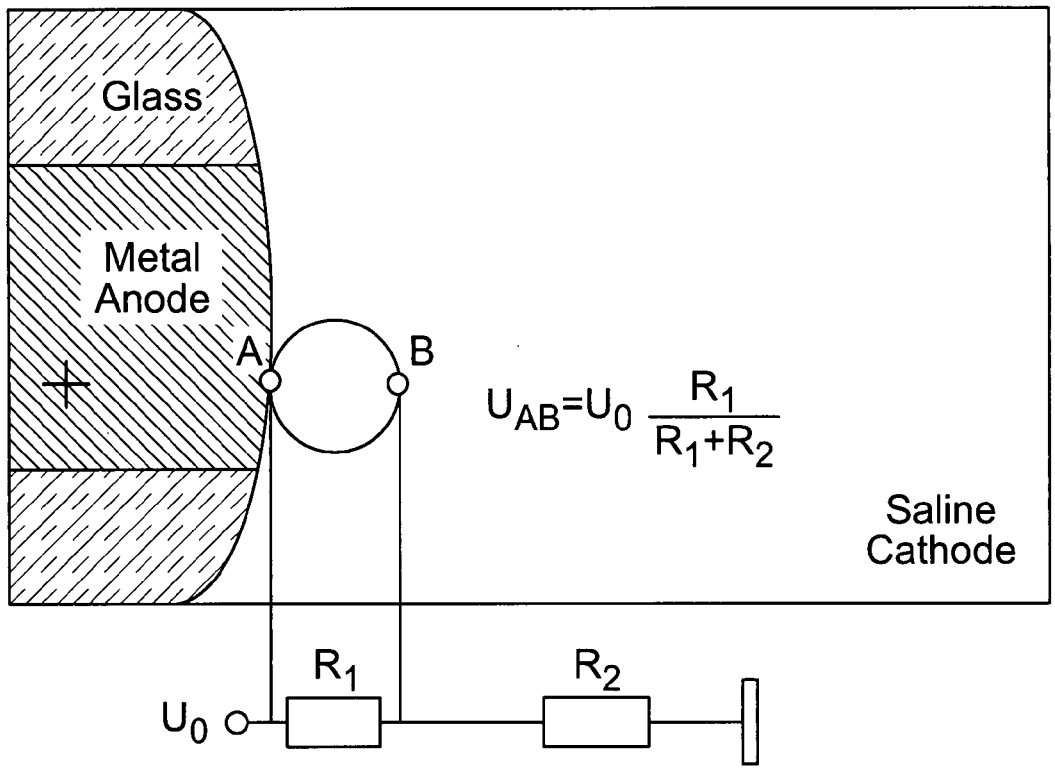
FIGS. 7A-7C show a sequence illustrating the initiation of an electric arc. The electrode shown has a cutting edge profile surrounded by an insulator that is between approximately ½ (half) and three times the thickness of the edge profile of the electrode.
Figure 7B:
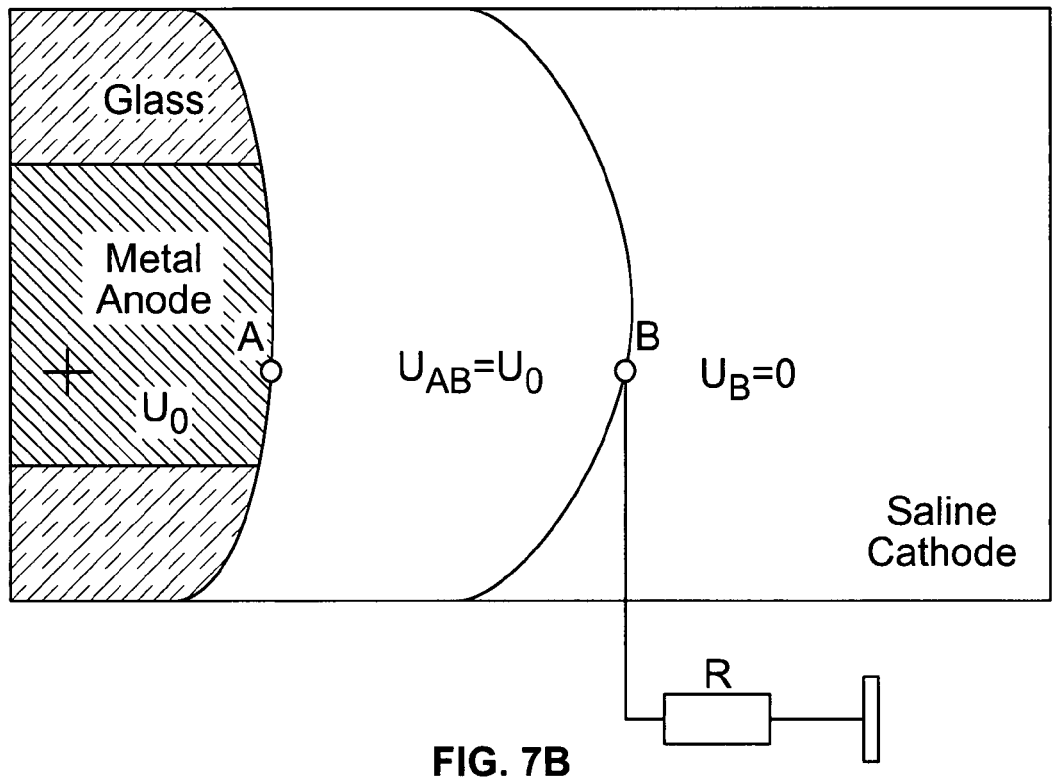
Figure 7C:
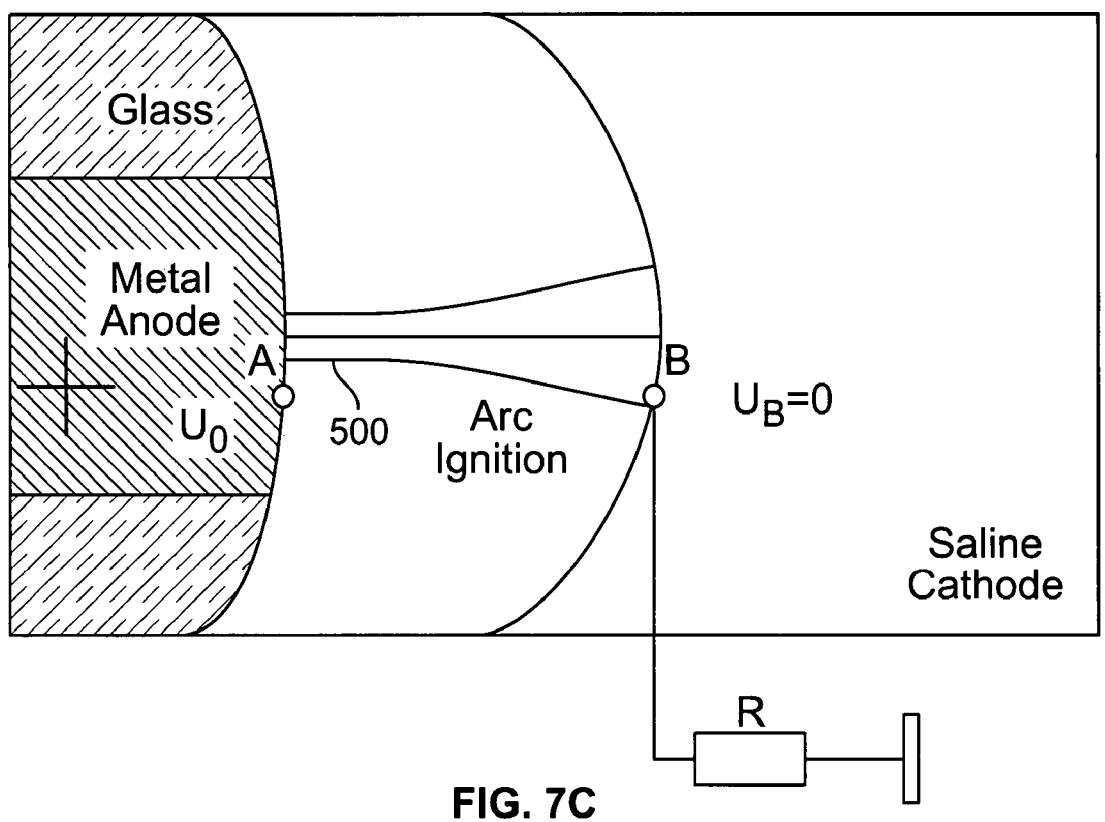

After the vapor cavity covers the entire electrode, with the proper level of the electric field, ionization of the vapor can occur. FIGS. 7A-7C illustrate the start of electric discharge in a saline solution. In FIGS. 7A-7C, the electrode is a metal anode, glass serves as an insulator, the saline solution is the liquid conductive medium, and a cathode is immersed in the saline solution. FIG. 7A shows the early formation of a vapor cavity in the saline solution. $R_1$ is the resistance from an equipotential through point A to an equipotential through point B. $R_2$ is the electrical resistance from the equipotential through point B to the cathode. $R_2$ is typically much larger than $R_1$, because not all of the anode is blocked by the vapor cavity. Thus, only a small fraction of the anode potential $U_{AB}$ (i.e., $U*R_1/(R_1+R_2)$) is present across the vapor cavity. In other words, the saline alongside the vapor cavity acts as a shunt resistor and thus the voltage drop across a vapor cavity is small until the vapor cavity completely covers the electrode.

FIG. 7B shows the vapor cavity at a later time in which it has grown to completely encompass the anode. Therefore the entire anode potential U is present across the vapor cavity, since current flow is blocked by the vapor cavity. FIG. 7C shows ignition of an electric discharge 500 inside the cavity. When the electrical potential different from A to B exceeds the ionization threshold for the vapor cavity, the gas in the vapor cavity ionizes and current flows from the electrode, across the vapor cavity to the conductive liquid medium. Preferably, the anode voltage U is selected so that U is greater than the ionization threshold for the complete vapor cavity of FIG. 7B, and $U*R_1/(R_1+R_2)$ is less than the ionization threshold of the partial vapor cavity of FIG. 7A. Selection of the anode voltage according to this condition ensures that the partial vapor cavity of FIG. 7A does not break down until it has grown to completely cover the anode.

Ideally the bubbles formed during this process grow slowly, on the order of tens of microseconds, so that the maximum velocity associated with bubble growth is below about 10 m/s. Such slow growing bubbles are not as mechanically damaging as cavitation bubbles that have maximum velocities on the order of 100 m/s. In addition, small bubbles are preferred to further minimize mechanical damage at the boundary of the surgical cut.

In applications that involve the cutting of biological tissue, ionization begins and the discharge is predominant in front of tissue, i.e., in the areas where tissue is located closer to electrode than the boundary of the vapor cavity in liquid. Therefore, using this approach, the uniformity of the original electric field is not critical because the tissue will only be exposed to electric current after ionization of the vapor cavity, which will occur substantially uniformly along the vapor cavity. For minimization of electroporation-related damage a burst of pulses could consist of pairs of symmetric bi-phasic or charge-balanced pulses, as described above.

With high electric fields, when ionization of water begins before vaporization, or when vapor cavity is ionized immediately after its formation, the disconnect of electrode from liquid may not occur and thus this process of sequential creation of multiple vapor bubbles along the electrode may not work.

Combination of Sharp Edge with a Burst of Pulses

The cutting electrodes described herein may work particularly well with an applied voltage (or current) regime having a very low duty cycle that includes busts of pulses (or busts of minipulses) that are repeated, as described above. FIGS. 13A-13E show exemplary stimulation regimes that may be used with these cutting electrodes, and are described below. The cutting electrodes described herein are not limited to use with these low duty-cycle stimulation regimes, however, and may be used with more traditional electrosurgical stimulation systems as well. For example, any of the cutting electrodes described herein may be used with continuous stimulation, high electric field, high voltage stimulation, etc. Although may of the advantages (particularly for low erosion rates and precise cutting) may be realized with the low duty-cycle stimulation described above, these cutting electrodes may also provide advantages for cutting at virtually any stimulation regime.

A burst of pulses can be applied for vaporization of liquid along a sharp (e.g., thin) edge of a disk or blade electrode. If a sharp edge is produced along a blade that has a singular point at its apex then ordinarily, the advantage of an enhanced electric field associated with the sharp blade edge may be tempered by the nonuniformity of the field caused by the apex. However, by using the approach described above for vaporizing the region along the electrode prior to ionizing the vapor bubble the problem of the field non-uniformity can be fixed. A sharp blade edge may provide field enhancement that leads to a smaller damage zone and lower threshold energy and is mechanically supported by the thicker part of the insulated blade. The apex with an associated strong field can be neutralized by application of a burst of pulses of appropriate duration.

Figure 13A:
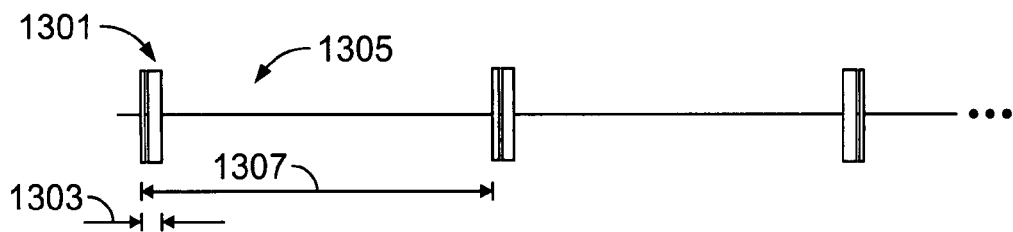
FIGS. 13A-13E show exemplary stimulation regimes that may be used with any of the electrosurgical blade electrodes described herein.

In addition to the stimulation regimes (e.g., low duty-cycle pulse regimes) previously described, FIGS. 13A-13E show different low duty-cycle stimulation regimes that may be used with any of the thin (or sharp) edged cutting electrodes described herein. FIGS. 13A-13E illustrate low duty-cycle pulse regimes that may be used to cut tissue. In FIG. 13A, the stimulation regime consists of repeated bursts 1301 of minipulses. A burst of minipulses may also be referred to as a pulse or a burst. Each burst of minipulses has a minipulse duration 1303, and is separated from the next burst of minipulses by an interburst interval 1305. Thus, the bursts of minipulses are repeated at a repetition rate ("rep rate"). A few examples listed below illustrate the values for the rep rate, and minipulse burst duration for various low duty-cycle pulse regimes. For example, a pulse regime for a low-duty cycle of less than about 10% duty cycle may have a rep rate of between about 10 Hz and 1 KHz (e.g., an interburst interval of approximately 1 ms to 100 ms), and a minipulse burst duration (pulse duration) of between about 10 μs and 100 μs. In some variations, a pulse regime for a low-duty cycle of less than about 10% duty cycle may have a rep rate of between about 10 Hz and 500 Hz and a minipulse burst duration of between about 10 μs and 200 μs. An exemplary pulse regime for a low-duty cycle of less than about 2.5% may have a rep rate of between about 10 Hz and 250 Hz (e.g., an interburst interval of approximately 4 ms to 100 ms), and a minipulse burst duration (pulse duration) of between about 10 μs and 100 μs.

Figure 13B:
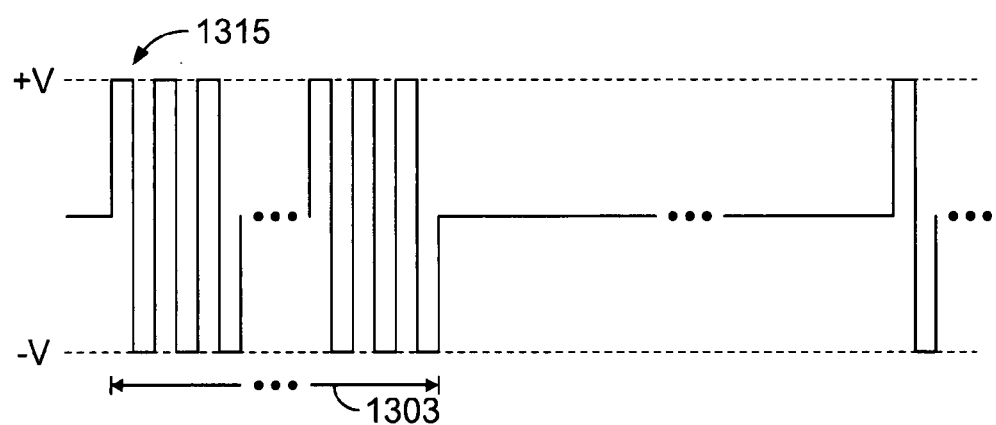
Figure 13C:

FIG. 13B shows a magnified view of the burst of minipulses 1301 within a low duty-cycle pulse regime. The burst of minipulses includes a plurality of minipulses 1315. In FIG. 13B, the minipulses are each identically shaped. The minipulses may have different pulse shapes. Each of the minipulses shown in FIG. 13B are bipolar minipulses, so that each minipulses have a positive and a negative voltage component (+V and −V). In some variations, the minipulses are not bipolar, but are monopolar, or have alternating polarities. FIG. 13C illustrates a burst of pulses 1316 that are not bipolar. The minipulses in FIG. 13B are also not separated by an intraburst interval (e.g., the time between minipulses is 0 s). Thus, the burst of minipulses in FIG. 13B is a continuous burst of minipulses, within the burst. In some variations, there is an intraburst interval that is non-zero. Fore example, the intraburst interval may be between 10 ns and 50 µs.

The duration of each minipulse within the burst of minipulses may be selected from an appropriate range, as previously described. For example, in some variations, the duration of the minipulse is between about 10 ns and about 10 µs. Other values of minipulse duration, duration between minipulses (intraburst interval) and the number of minipulses may be used and still maintain the low duty-cycle nature of the stimulation regime. The minipulses within each minipulse burst may have any appropriate voltage, as described above, particularly for the initiation and maintenance of plasma. For example, the voltage may be between about ±600 V, or between about ±500 V, or between about ±400 V.

Figure 13D:
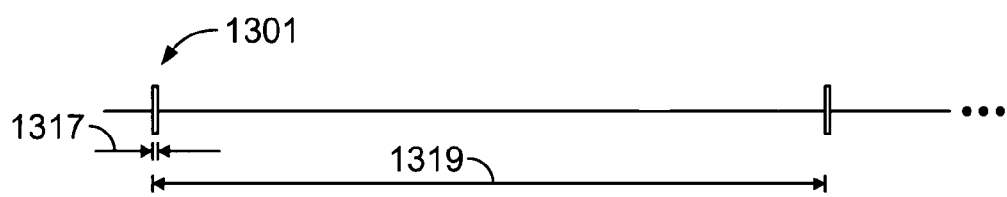
Figure 13E:
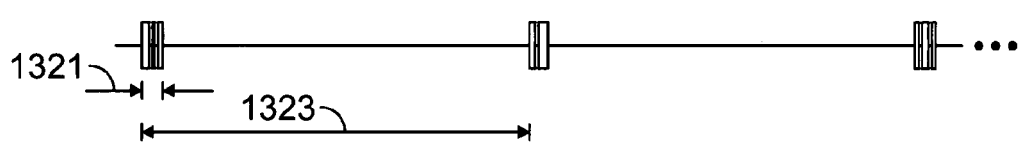

FIG. 13D shows an example of a pulse regime having a duty cycle of less than 1% (e.g., 0.01%). In this example, the minipulse burst duration 1317 is approximately 10 µs, and the rep rate 1319 is approximately 10 Hz. The minipulses within the burst are bipolar, and are continuous. FIG. 13E is another example of a low duty-cycle pulse regime. In this example, the duty cycle is approximately 5%. The burst duration 1321 is approximately 100 µs, and the rep rate is approximately 500 Hz.

Figure 8A:
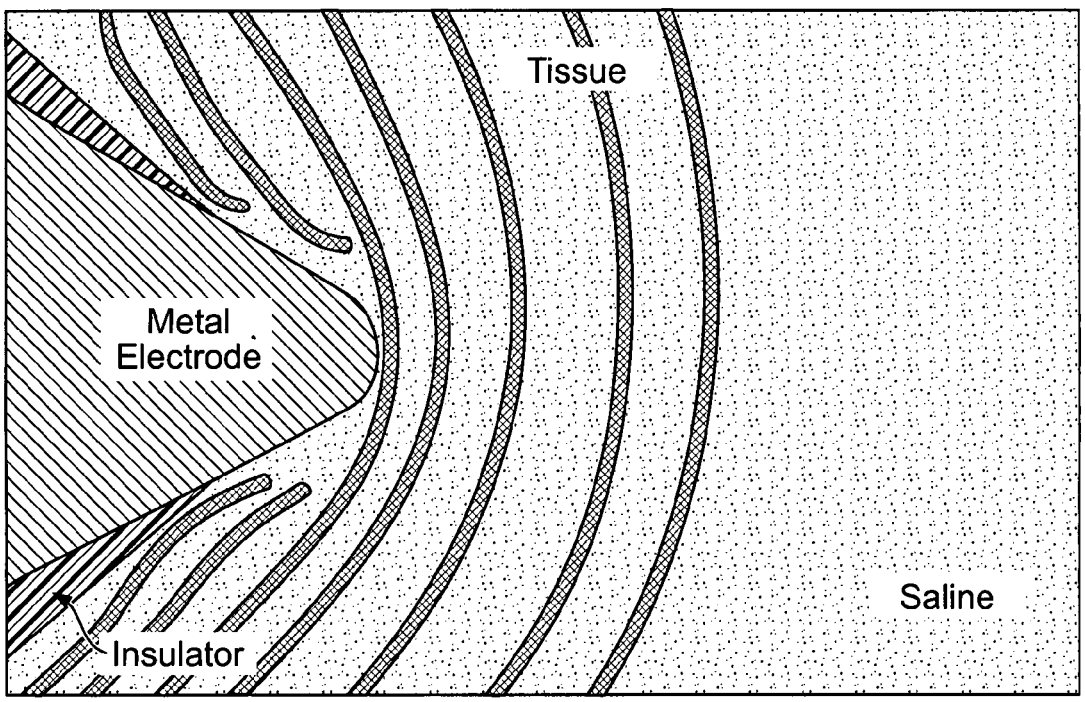
FIGS. 8A-8D show electrodes as a blade edge and biological tissue immersed in saline.
Figure 8B:
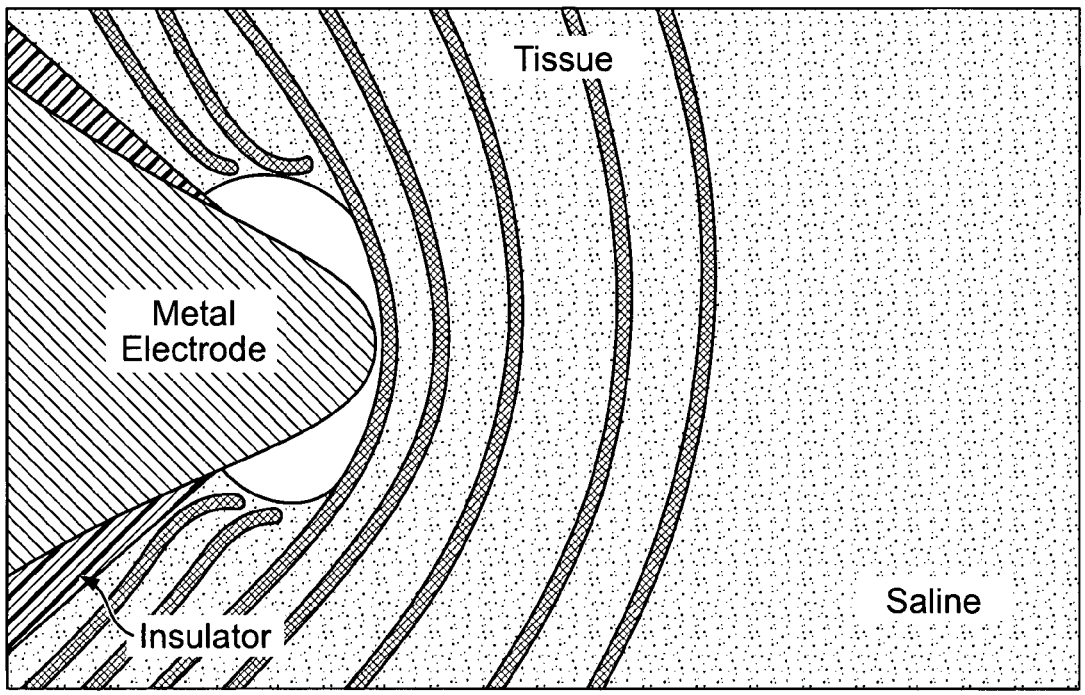
Figure 8C:
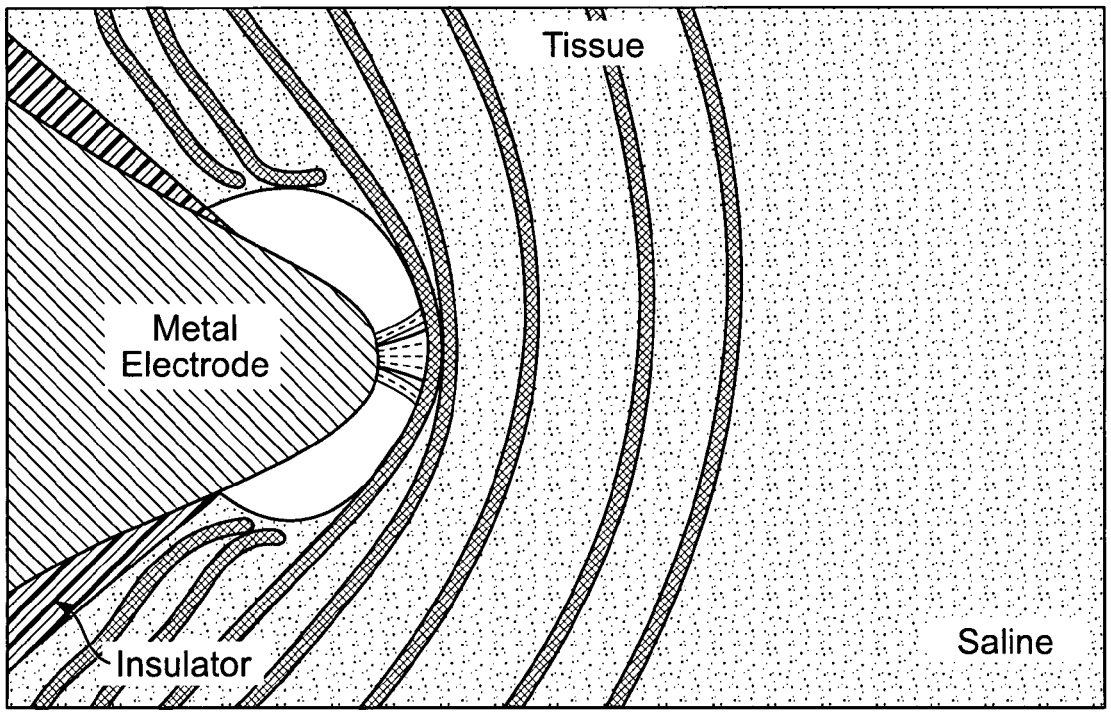
Figure 8D:
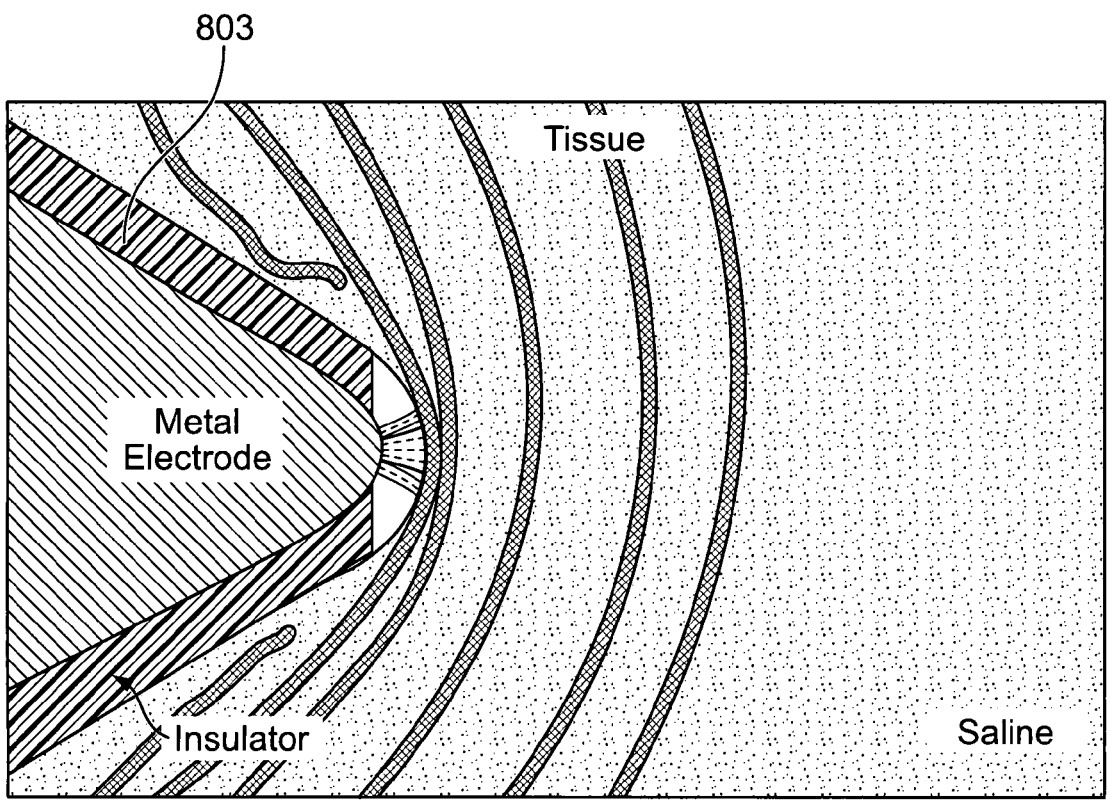

Returning now to FIGS. 8A-8D, the effect of any of the pulsed stimulation regimes (including the low duty-cycle regimes) described above is illustrated. FIGS. 8A-8C show the use of a pulsed electric field to first generate a vapor bubble around one example of a sharp blade edge and then produce an electric discharge from the blade to the targeted biological tissue by ionization of the vapor. FIG. 8A shows the blade electrode before the vapor cavity is formed. In this example, the insulator is spaced from the edge (curved region) of the metal electrode. FIG. 8B shows a vapor cavity forming over the portion of the blade electrode not covered by the insulator. When the electrical potential is high enough, an electric discharge occurs between the blade electrode and the tissue as shown in FIG. 8C. As shown in FIG. 8C, the discharge is concentrated in the region of smallest separation (least resistance) between the electrode and the tissue. A similar effect is seen in the electrode of FIG. 8D. In FIG. 8D, the insulator 803 extends to the edge of the conductive metal blade electrode, and has a somewhat uniform thickness up until the exposed edge region. This thickness is between about one-half and three times the thickness of the exposed metal edge. The formation of the vapor cavity and the electric discharge in this example is nearly identical to that in the example shown in FIGS. 8A-8C, however, the size of the vapor cavity may be substantially smaller.

As described briefly above, the dimensions and thickness of the electrode may allow for more uniform erosion of the cutting (e.g., blade) electrode, and may also be easily fabricated. Cutting electrodes having uniform erosion may be referred to as "self-sharpening" because they do not dull with repeated use, as the blade erodes, but my retain the blade profile.

Self-Sharpening of the Edge of a Blade Electrode During Use

A thin electrode may be rapidly etched during use. Such a thin (or sharp) blade edge of a blade electrode may also be rapidly etched in use, as described above. Rounding the edge by etching, i.e., increasing the edge radius of curvature, may lead to an increase in the threshold voltage and pulse energy, which in turn, will increase the extent of the collateral damage zone. To prevent this effect, the cutting electrode may be configured to provide "controlled etching," leading to self-sharpening can be used Etching is most efficient inside the zone of evaporation (i.e., the vapor bubble). Therefore, the region of most efficient etching can be determined by parameters of the driving waveform, which determine the size of the vapor bubble. Uniform erosion can be achieved by sizing the vapor bubble to include the tapering region near the blade edge. In such a case, efficient etching occurs over the entire tapering region, and the blade edge can be maintained with an approximately constant edge radius of curvature. Optimal width of the etching zone is determined by the thickness of the blade and the desirable tapering angle. For a blade of thickness D outside of the tapering region, blade tapering angle α, and edge radius of curvature $r_0$, the tapering region extends a distance $r_0+(D/2-r_0)/\tan(\alpha/2)$ inward from the end of the blade edge. Ideally the vapor bubble should extend at least this far inward from the end of the blade edge. Such a uniform erosion regime keeps the electrode functional for a long time despite the erosion. Alternatively, blade 100 can be slideably mounted between insulators 210 and 220 such that erosion of blade 100 during operation can be compensated by extending a fresh section of blade 100 from between insulators 210 and 220.

Figure 9:
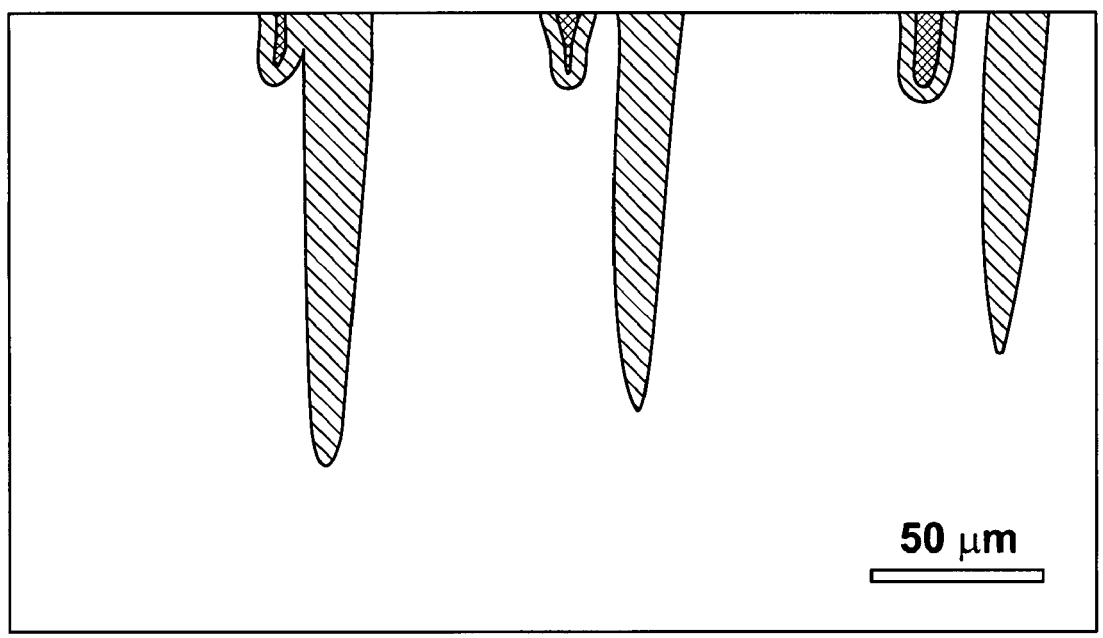
FIG. 9 shows that etching of a 15 µm-thick Tungsten blade by electric discharges at surgical settings leaves the blade edge sharp as it shortens.

As described in greater detail below, fabrication of a blade having uniform erosion can be simplified by using the electrical discharge itself to remove the insulators from the blade surfaces near the blade edge. Preferably, the blade is milled to achieve an appropriate blade tapering angle either before, or immediately after the blade surfaces are covered with thin layers of insulators. The blade is immersed into a conductive medium and electrical pulses are applied with waveform parameters similar or identical to those appropriate for electrosurgery. The electrical discharge at discontinuities will break and remove the insulator from the active surfaces of the electrode, but in other areas the insulator will remain intact. As the blade edge is etched during use, the insulator in its proximity will be removed as well. FIG. 9 shows the etching of a Tungsten blade by discharges at pulse settings that would be appropriate for surgical cutting. The edge remains sharp as the blade gets shorter.

As described above, the cutting electrodes described herein are generally, thin insulated electrodes. These cutting electrodes, which may also be referred to as electrosurgical blades (or blade electrodes), may be insulated so that only the active edge of the electrically conductive region is exposed. exposed cutting edge may be particularly thin (e.g., less than 100 µm, or less than 50 µm, or less than 20 µm thick). The blade may be adapted to have uniform erosion during operation. Thus, one or more insulation layers may surround the active edge of the blade. The thickness of the material and/or the composition of the material may be chosen so that the rate of erosion of the surrounding insulator is matched to the rate of erosion of the conductive blade (electrode). Described below are exemplary electrosurgical blades that implement the design principles described above.

The exposed cutting surface of the electrodes described herein is typically less than 100 µm in thickness. For example, the exposed cutting surface may have a thickness that ranges between about 10 µm and 100 µm, or 10 µm and 50 µm, or 10 µm and 30 µm, or 10 µm and 20 µm, or 15 µm and 50 µm. As mentioned above, the thickness of the cutting surface may be the thickness between an upper and lower surface of the conductive metal blade region. The thickness may be the thickness of the cutting edge, which may be curved or flat between the upper and lower surfaces of the conductive metal blade. For example, FIGS. 8A-8D show a rounded exposed edge thicknesses. and FIGS. 7A-7C show a somewhat flat edge thickness.

In general the cutting surface may also have any appropriate length. Returning to FIGS. 8A-8D and FIGS. 7A-7C, the length is not shown, but extends perpendicular to the plane shown in the figures, either up from the page, or down into the page. FIG. 4B shows a partially cut-away perspective view of the end of a cutting electrode, showing the length extending from the cut-away region. In some variations, the length of the cutting surface (also referred to as the length of the active edge) is curved, or shaped (e.g., V-shaped, L-shaped, etc.). The thickness of the edge along the length may be constant, or it may vary. The length may be straight. The length may be short (e.g., less than 1 mm), or it may be long (e.g., greater than 2 mm, greater the 5 mm, greater than 10 mm, etc.). In some variations, the length is less than about 500 µm, less than 1 mm, less than 2 mm, less than 5 mm, less than 10 mm, etc.

In some variations of the electrosurgical blades an insulator surrounds the active edge of blade electrode. FIGS. 7A-7C show a cross-section through a blade electrode having such a blade profile. In FIGS. 7A-7C, the insulator abuts the edges of the cutting electrode (marked "metal anode") on both sides. In this example, the insulation is glass (e.g., glass enamel). The thickness of the insulator is the combined thickness of both the upper and lower glass insulators, and is approximately the same thickness as the metal anode (e.g., 1× the thickness of the active edge of the electrode). As described herein, the thickness of the insulator around the exposed edge typically ranges from between about one half and three times the thickness of the exposed active electrode region, so that the electrical discharge (e.g., plasma and heat) at the active end etches both the metal and the insulator uniformly.

Figure 10A:
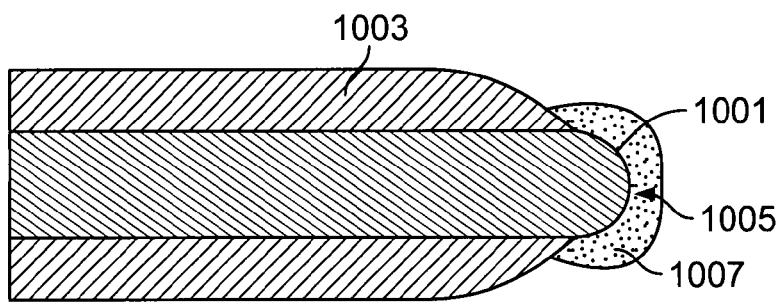
FIGS. 10A-10D illustrate erosion of different insulation and conductive regions of electrodes.
Figure 10B:
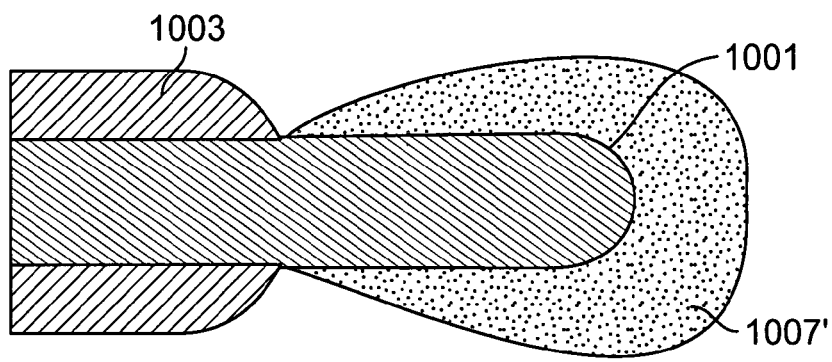
Figure 10C:
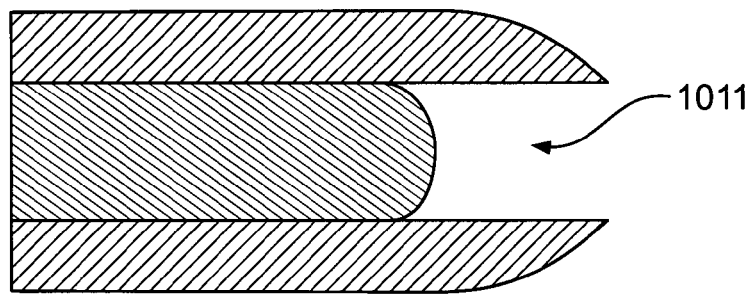
Figure 10D:
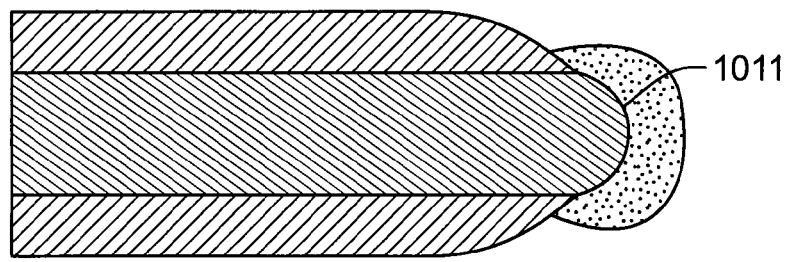

The exposed (uninsulated) edge of the cutting electrode may be referred to as the distal end of the electrosurgical blade. The region of the cutting edge of the electrosurgical blade extending proximally from the distal end may be referred to as the erodible depth of the cutting electrode. The profile the region behind (or adjacent) to the exposed cutting edge may have the same blade profiled. For example, the length and thickness of the edge of the electrosurgical blade (the conductive region forming the edge bade as well as any adjacent insulation) may be approximately the same as the length and thickness of the exposed edge of the electrosurgical blade. Thus, the electrosurgical blade may have an erodible depth that has approximately the same blade profile over a predetermined length (e.g., for 10 µm, 20 µm, 30 µm, 40 µm, 50 µm, 100 µm, 200 µm, or more). Thus, as the exposed edge region (including both the conductive edge and the surrounding insulation) is eroded, the relative thicknesses of the cutting edge and the adjacent insulation will remain constant over the predetermined distance. This may allow for a relatively constant electric field, as described above, and for more uniform cutting, thereby extending the lifetime of the blade. Referring to FIG. 10D, the erodible depth is shown is indicated by the line 1011.

In some variations, the blade profile over this erodible depth is not identical to the exposed or active blade profile, but has the same ratio of the thickness of the electrode and the thickness of the surrounding insulator. For example, the thickness of the insulator in this region is still between one-half and 3 times the thickness of the active electrode over the erodible depth.

The active conductive region of the cutting electrode may be any appropriate electrically conductive material, as described above. For example, the conductive material may be made of a metal, a conductive ceramic, or a conductive plastic. The active electrode may be formed from a conductive metal such as gold, titanium, tantalum, molybdenum, tungsten, stainless steel, etc., and particularly thin foils of such metals. Thus, the foil may have the thickness, length and erodible depth of the final electrode, and insulator may be applied onto the foil (a support or shield may also be used to form the electrosurgical blade, as described below). For example, the active electrode forming the cutting edge may be made from a foil such as 15 µm-thick titanium foil. In some variations, the conductive material forming the active electrode is formed by plating or evaporation onto a substrate (which may include an insulator), rather than being formed from a foil.

Any appropriate insulation may be used with the blade electrodes described herein. Thus, the insulator may be formed of a ceramic (including glass), a plastic, or the like. In particular, insulators that are matched to the conductor used to form the active electrode may be preferable. Exemplary insulators include glass, polytetrafluoroethylene (e.g., Teflon), and silicones. More than one insulator may be used. For example, multiple thin layers of insulators may be used, and/or different regions of the electrosurgical blade electrode may be insulated with different insulators. Alumina ($Al_2O_3$) has been used as an insulator in electrosurgical device, and may be used in the devices described herein as well. However, glass may be superior to alumina because glass is more ductile, and can be applied in very low thicknesses (e.g., as low as 5 µm) and is very cost effective (alumina is typically only applied in thicknesses of greater than 0.25 mm). Although alumina is brittle, it (like glass) has a high thermal resistance to erosion, good dielectric strength, and is biocompatible. An insulated cutting electrode having a balanced erosion rate may be formed by matching the material properties and dimension of the insulator to the material properties and dimensions of the active surface. This is illustrated in FIGS. 11A-11D, which shows erosion of different electrodes that may be operated for electrosurgical cutting of tissue.

Figure 11A:
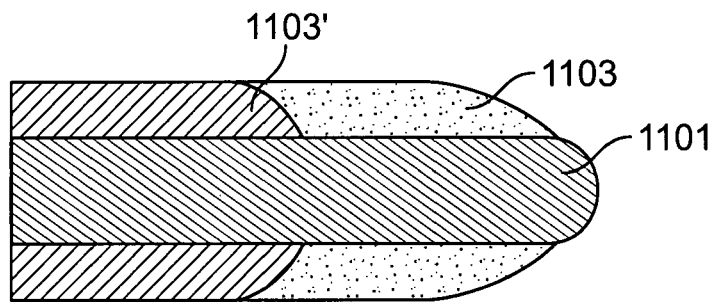
FIGS. 11A-11D show erosion of different electrosurgical cutting electrodes.

FIG. 11A shows the cutting profile of an electrosurgical blade having an active metal electrode (e.g., titanium) that is insulated with a thin layer of insulation that erodes much faster than the active electrode (a 'soft' insulation). For example, the insulator shown in FIG. 11A may be a plastic or other material with a relatively low melting and vaporization or pyrolisys temperature that melts (or vaporizes) and erodes faster than the metal electrode that it is insulating. For example, a titanium foil electrode may be etched by plasma-mediated discharge at a rate of about 2 µm per minute of operation (e.g., 12.5 µm titanium foil stimulated at 535V, at a duty cycle of 0.6%). Etching rates may increase linearly with duty cycle and can reach 0.3 mm per minute with a continuous RF waveform (e.g., duty cycle=100%). In FIG. 11A, the lighter insulated region 1103 shows the position of the insulator before stimulation, and overlaid on top of this is a darker region 1103', showing the position of the insulator after a period of stimulation. In this example, the electrode 1101 has not significantly eroded, but the insulator has eroded to leave the metal exposed, and has increased the effective active surface of the cutting edge. This situation was also described above for FIG. 10B.

Figure 11B:
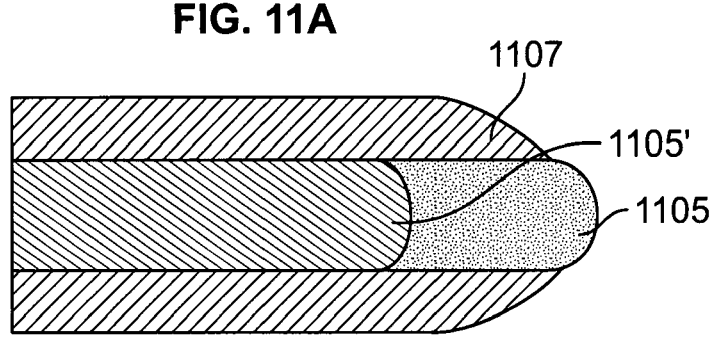

FIG. 11B shows the effect of an insulator 1107 that erodes much more slowly than the conductive active electrode 1105, 1105' that it insulates. Before stimulation the electrode 1105 is surrounded by the insulator 1107. After a period of stimulation, the active electrode has eroded 1105', while the insulator 1107 has not substantially insulated. In this example, the insulator may be a substantially 'hard' material such as a ceramic that does not soften, melt or vaporize substantially at the temperatures of the plasma formation. This example was also described for FIG. 10C, above.

Thus, the material properties of the insulator may be matched to the material properties of the active electrode. For example, the local temperature of the bulk electrode during electrosurgical cutting (e.g., plasma-mediated discharge) may be approximately 800° C., which is sufficient for melting many materials. In some variations the softening, melting or vaporization temperature of the insulator may be approximately 800° C., or slightly higher than 800° C. (or slightly less than 800° C.) in order to help achieve uniform erosion of the active electrode and insulator, thereby maintaining the profile of the cutting electrode.

Glass insulation materials may be particularly useful for insulating the electrosurgical blade electrodes described herein. In particular, glass enamels, which may be applied as a fluid or suspension to an appropriately thin coating, may be used. Enamels that are biocompatible (e.g., do not contain lead or other potentially harmful materials) may be particularly advantageous. For example, Thompson enamel 1010 (720° C. grade, white, lead-free) enamel may be used. Described below are methods of making that illustrate materials including enamels that may be used to insulate any of the cutting electrodes described herein. As mentioned, other types of insulation materials may be used, including ceramics.

In some variations more than one insulation material is used. For example, a first insulation coating may be applied to the active electrode, and a second insulation layer may be applied to the first insulation layer. Different regions of the electrosurgical blade electrode may have different insulation. The material properties of the different insulation layers may be different. For example, the insulative property of the first and second insulator may be different, the thermal properties of the different insulators may be different, the hydrophobicities may be different, etc. For example, in some variations, the first insulator comprises glass, and the second insulator comprises polytetrafluoroethylene (Teflon). An outer coating of Teflon on the device (particularly the blade) may reduce surface friction.

Figure 11C:
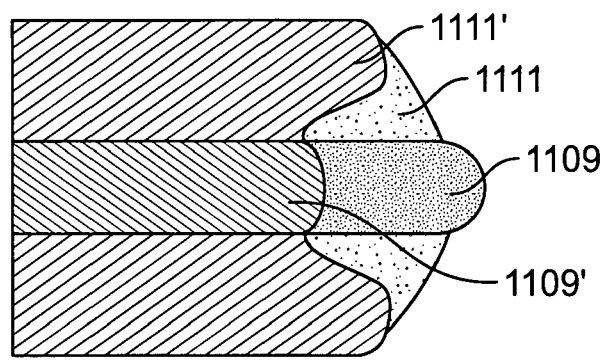

The dimensions of the active electrode and the surrounding insulator may also be matched to help achieve uniform erosion of the cutting electrode profile. For example, the thickness of the insulation layer may be matched to the thickness of the exposed active electrode edge, as shown in FIG. 11C. In FIG. 11C, a relatively thick layer of initial insulator 1111 surrounds the cutting electrode 1109. Before stimulation, the electrode 1109 and the surrounding initial insulation 1111 are shown in light grey. During stimulation, both the electrode and the surrounding insulation are eroded at nearly the same rate (eroded electrode is 1109'), however, the eroded insulation 1111' further from the active region of the electrode is not eroded as rapidly, since it is further from the zone of electrical activity (e.g., plasma formation in some variations). This was described above as etching within the zone of evaporation within the vapor bubble formed. As described above, the size of this etching zone may depend on the applied energy (e.g., the stimulation regime), and the thickness of the active surface of the electrode. In general, this zone of etching may be approximated as less than three times the thickness of the active region. In some variations, the zone of etching is approximated as less than two times the thickness of the active region. Since the zone of etching may be centered on the active electrode, the thickness of the insulator surrounding the active electrode may be uniformly thick around the active electrode (e.g., on both sides of the active electrode). Thus, the total thickness of the insulator surrounding the active electrode should be less than three times the thickness of the active electrode, and is approximately the same thickness on both (or all) sides of the exposed edge of the active electrode in order to get uniform etching.

Figure 11D:
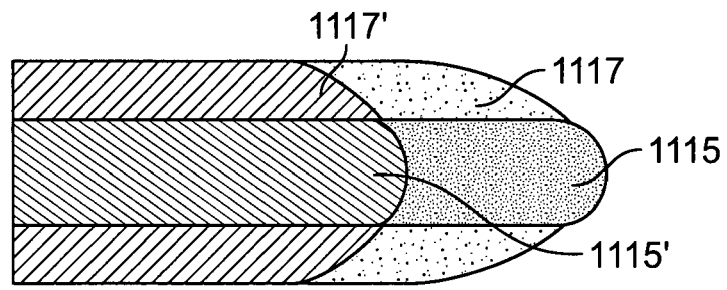

This may be seen in the example of FIG. 11D. In FIG. 11D, the erosion of the insulation and the erosion of the active electrode are matched so that during operation for electrosurgical cutting the blade erodes uniformly, without substantially changing the edge profile of the cutting edge. For example, the initial blade profile of the active electrode 1115 and the insulator 1117 are shown in light grey. After operation of the blade for electrosurgical cutting, the darker gray region shows the eroded profile of the electrode 1115' and the insulator 1117'.

In practice, the electrosurgical blades described herein may have a very thin uninsulated cutting edge (e.g., between about 10 µm and 100 µm, or about 10 and 50 µm, or approximately 15 µm, etc.) surrounded by a thin layer of insulator (e.g., between about half and about three times the thickness of the cutting edge (e.g., if the cutting edge formed from 15 µm thick foil, the insulation should be between about 7.5 µm and about 45 µm thick, in total). Thus, the blade profile may be very thin (e.g., less than 100 µm or thinner in some cases), and may extend for the length of the erodible depth (e.g., approximately 0.5 mm or more). Additional structure or materials may be applied for support. For example, the active electrode may be attached to a support that provides enhanced support to the device, and may facilitate attachment of the cutting edge to a handle or the like. Thus, the electrosurgical blade may include a handle or grip (including one or more switches for activating the device). In addition, the electrosurgical blade may also include one or more additional elements such as lighting sources (e.g., light guides, optics, fibers, LEDs, etc.), cameras, or the like.

The active or cutting edges of the electrosurgical blades described herein may be configured for specific uses. In some variations, the electrosurgical blades are configured as knifes, having elongated (curved or straight) lengths for cutting. In some variations, the cutting edge forms a shape that may be used with a specialized or specific application. For example, the cutting electrode may be a needlepoint electrode, a catheter (cardio) cutting electrode, an L-shaped electrode, a wire loop resector, part of a scissors, or the like. In some variations, the cutting electrode may include multiple (e.g., parallel) edges.

Figure 12A:
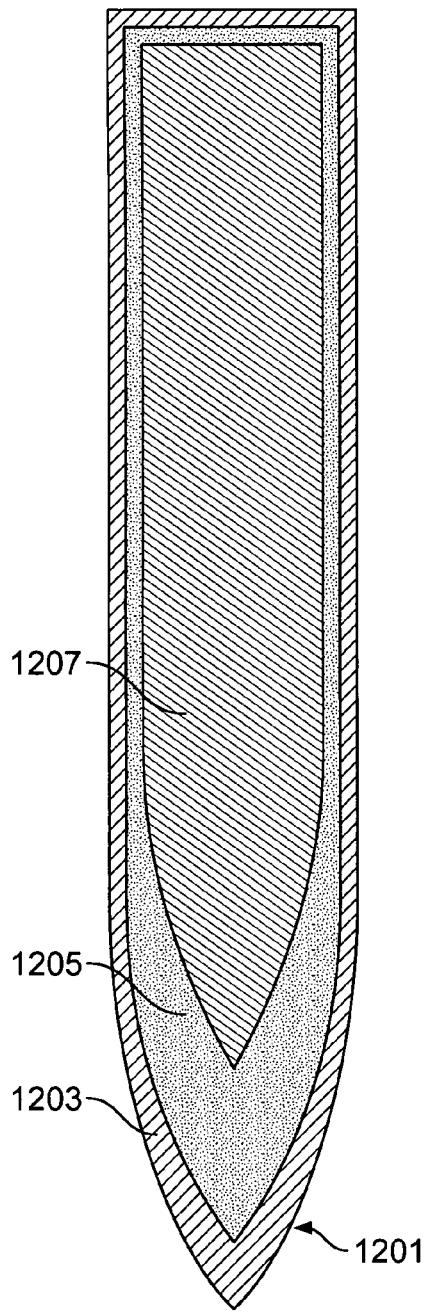
FIGS. 12A and 12B illustrate one variation of an electrosurgical blade electrode.
Figure 12B:
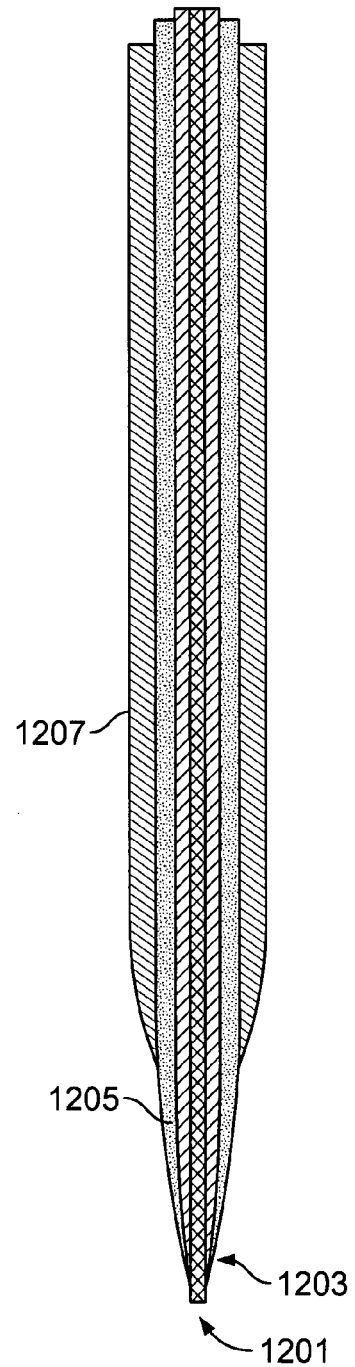

FIGS. 12A and 12B illustrate one variation of an electrosurgical blade electrode. In this example, the cutting edge 1201 is less than 100 µm thick. The cutting edge includes the uninsulated active edge of the electrode and the adjacent insulation (e.g., glass insulation). Immediately behind the cutting edge is the erodible depth 1203 which extends for about half a mm inward and proximal to the cutting edge. Support for the cutting edge may be provided by building up additional support using one or more support structures 1205, 1207 that can be layered on top of the electrode forming the cutting edge and the erodible depth to provide additional support. This support region may be insulated (e.g., the same insulator covering the cutting electrode may be applied over the support. The supports may themselves comprise an insulator.

Figure 14A:
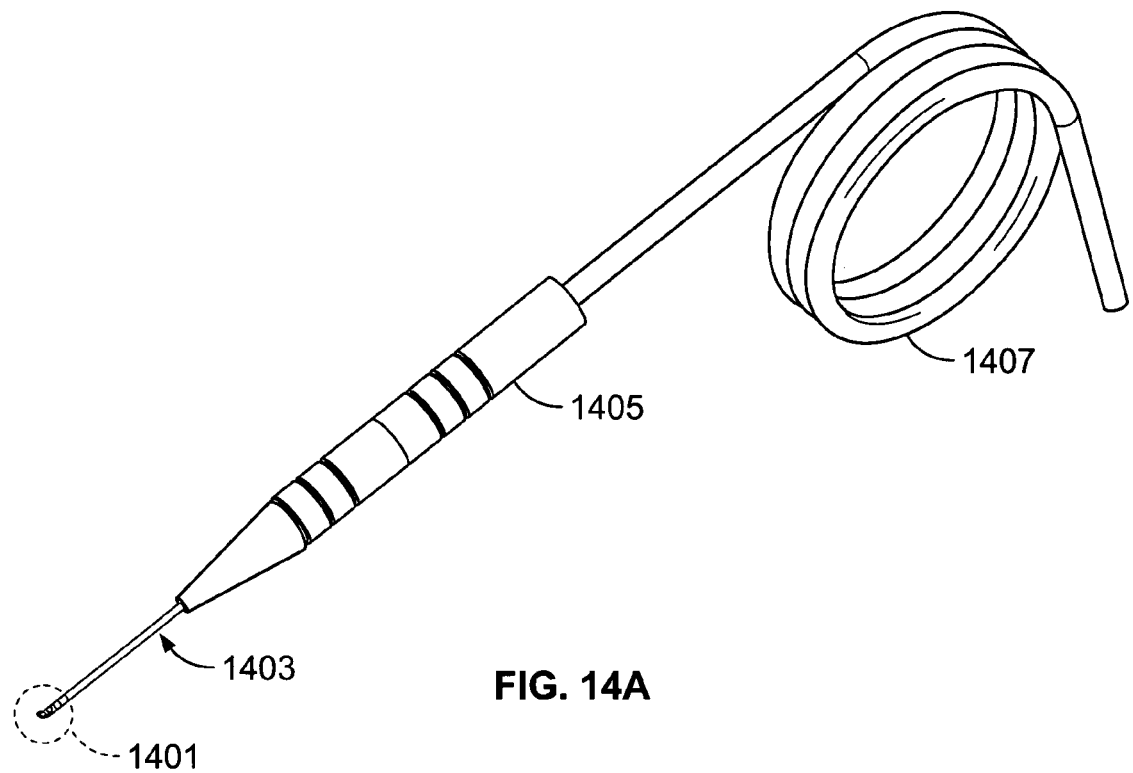
FIGS. 14A-14E show an exemplary electrosurgical blade electrode.

Another exemplary electrosurgical blade electrode is shown in FIGS. 14A to 14E. FIG. 14A shows the tip 1401, shaft 1403, handle 1405, and cable 1407 of one variation of an electrosurgical blade electrode for cutting biological tissue. The tip 1401 (shown in more detail in FIGS. 14B-14E) is located at the end of a shaft 1403. The shaft 1403 may be any appropriate length (e.g., between 20 and 50 mm) and extends from the handle region 1405. The shaft is typically insulated, as is the handle 1405. The handle may include one or more grip regions and may be configured to facilitate grasping of the handle (e.g., by including a texture or material for easy gripping). The cable 1407 connects to the proximal end of the handle and can extend so that it may be connected to a power source (e.g., voltage source). As mentioned above, a system including an electrosurgical blade may include a power supply or voltage source configured to provide electrical stimulation to the electrosurgical blade in any appropriate stimulation regime, including those described above (e.g., the low duty-cycle stimulation regimes).

Figure 14B:
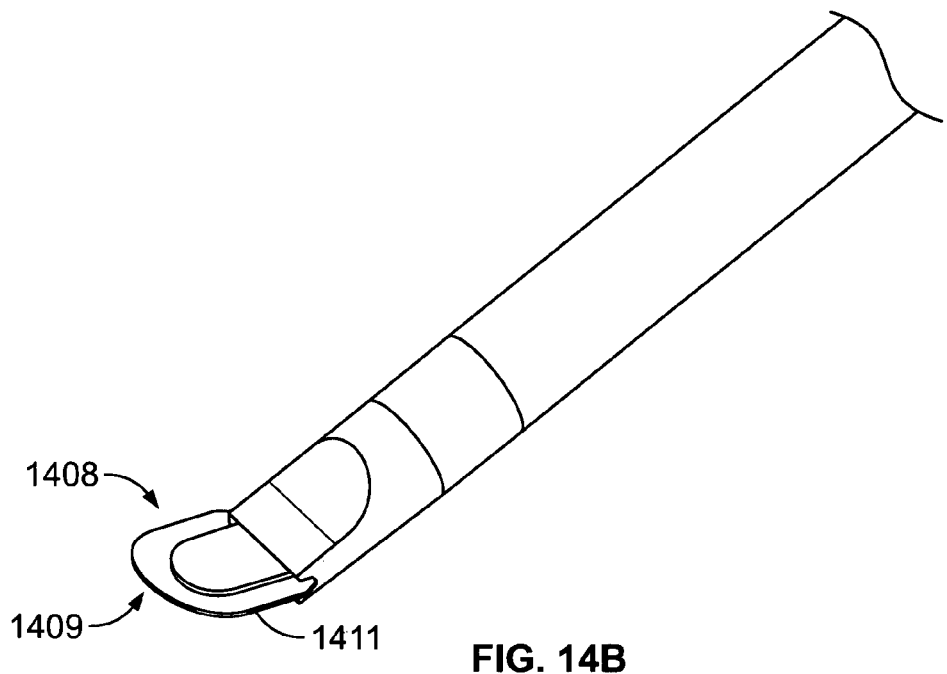
Figure 14C:
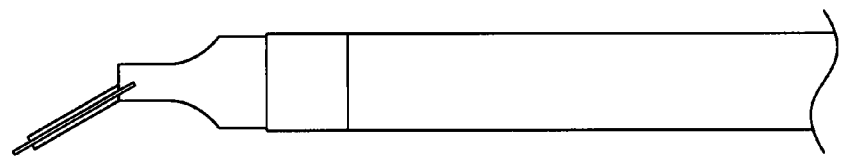
Figure 14D:
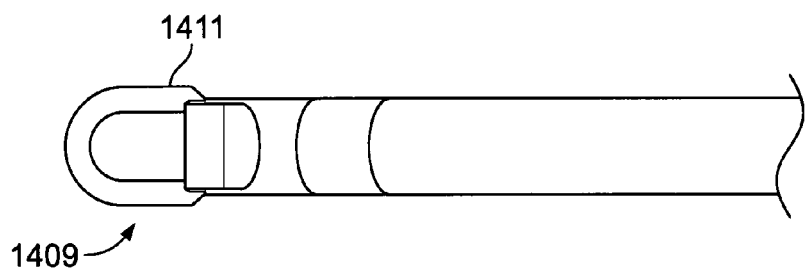

FIG. 14B is a magnified view of the tip 1401 of the electrosurgical blade indicated as region A of FIG. 14A. In this example, the tip region includes a cutting electrode 1408 that is angled with respect to the shaft 1403 and handle 1405, to facilitate cutting. The angle in this example is approximately 30 degrees, although any reasonable angle may be used. In some variations, the angle may be manually adjusted. This angle may be more readily seen in FIG. 14C. The dimensions shown in FIGS. 14C and 14D are intended only for illustration. Any appropriate dimensions may be used. The cutting electrode includes the cutting edge 1409 that is made up of the thin uninsulated active electrode surface and the adjacent insulator(s) that surround the active electrode surface.

The cutting edge 1409 of the cutting electrode 1408 (e.g., the blade profile) extends around the outer perimeter of the tip region in a U-like shape, as shown in FIGS. 14B and 14D. Immediately behind the cutting edge is an erodible depth 1411 of about 200 μm. The thickness of the electrode (cutting electrode) and the insulation layers surrounding the electrode above and below it is uniform, and equivalent to the thickness of the cutting electrode and adjacent insulation of the edge profile. Thus, the edge profile may remain substantially constant as the edge (insulation and electrode) erodes.

Figure 14E:
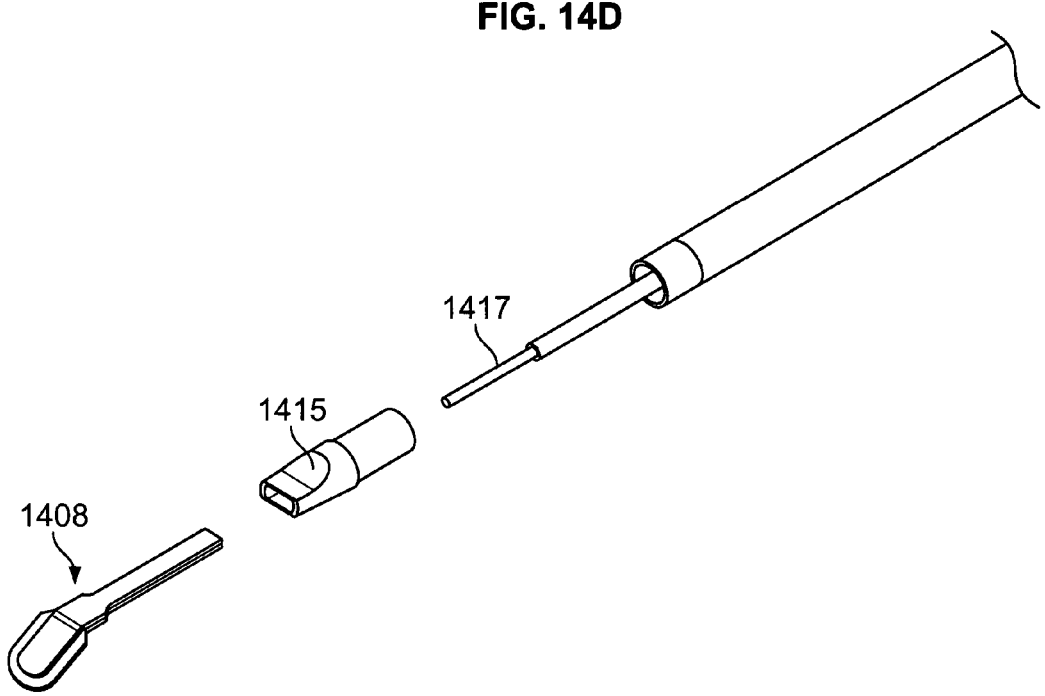

FIG. 14E shows an exploded view of the tip region 1401, including the cutting electrode 1408 that mounts into a holder 1415 and makes electrical contact with an electrical conductor (e.g., wire) 1417. This wire may be insulated and then passed through the shaft 1403, then the handle 1405, where it may eventually make an electrical contact with a power supply through the cable 1407.

Fabrication of Electrosurgical Blade Electrodes

Any of the electrosurgical blades described herein may be fabricated by applying a thin layer of insulation in one or more applications to thin layer of conductive material, particularly over the edge region (including the adjacent etchable depth region behind the edge itself) of the thin layer of conductive material. The conductive material typically has a thickness of less than 100 um, or less than 50 μm, or less than 30 μm. The insulator is applied to both sides of the substantially flat material so that the total thickness of the insulator material (when dry if it is added wet) is between about one-half and three times the thickness of the conductive material. In this example, "total" means that the sum of the thickness of the insulation on both sides (e.g., the top and the bottom) is between about one-half and three times the thickness of the insulator. As mentioned above, more then one insulator may be applied. The insulator may be applied over the entire thin layer of conductive material (including the edge region) or it may be applied up to the edge region.

Figure 15A:
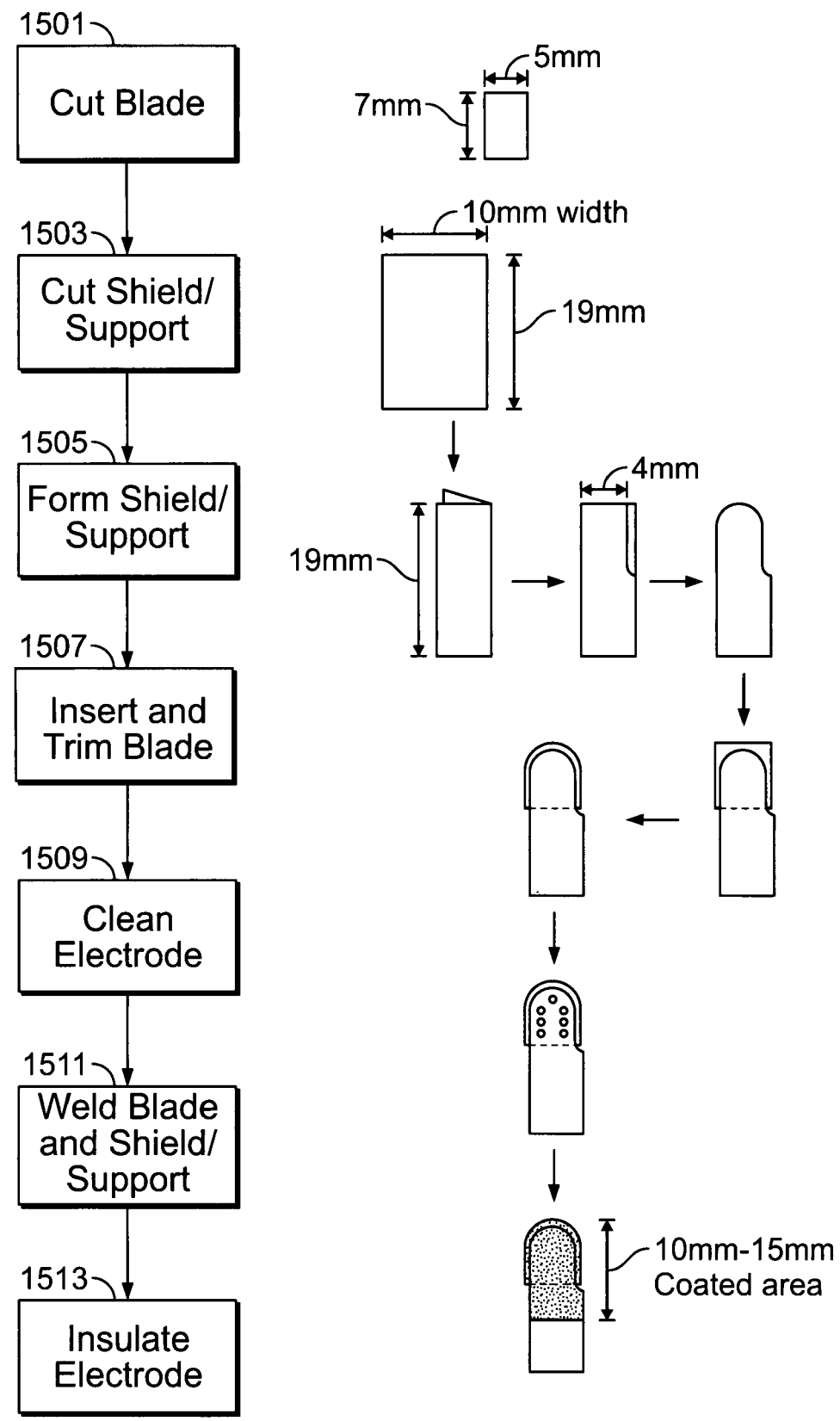
FIGS. 15A and 15B illustrate a method of fabricating one variation of an electrosurgical blade.
Figure 15B:
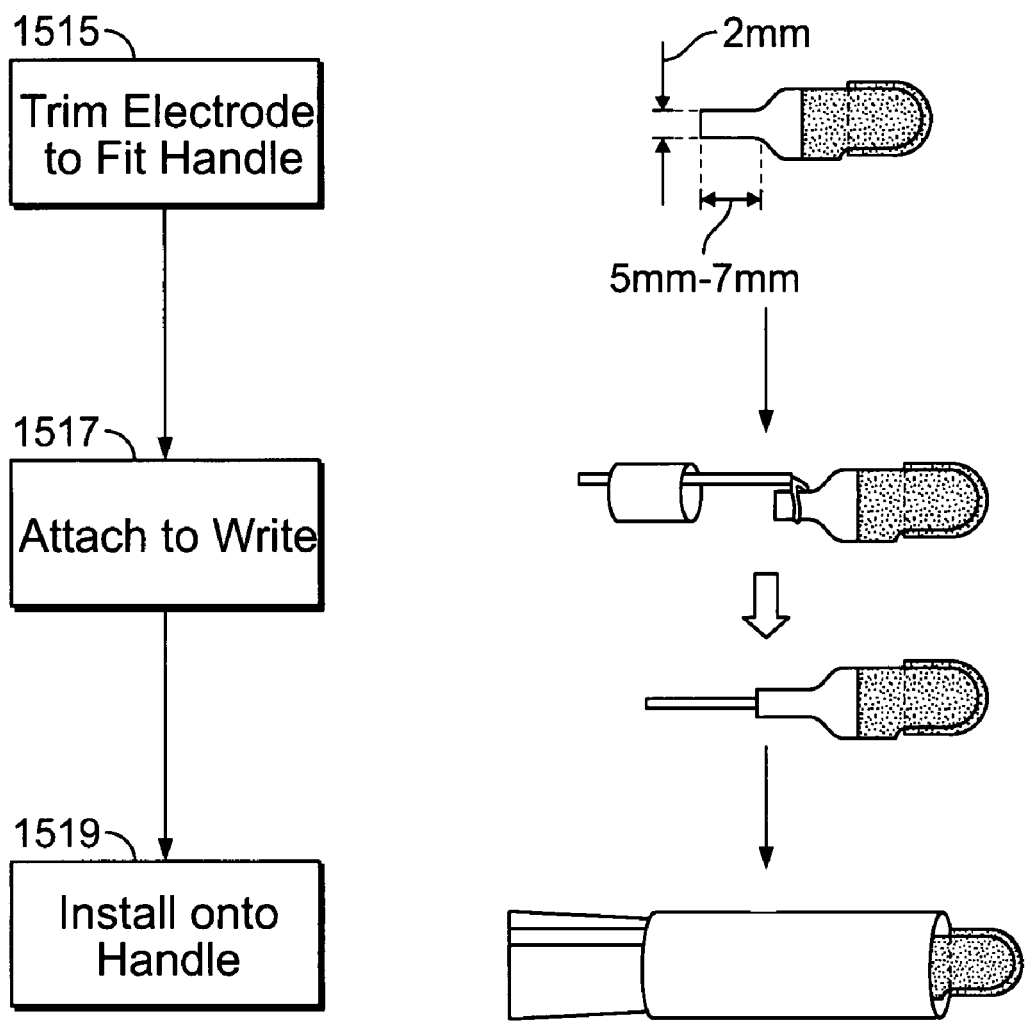
Figure 16:
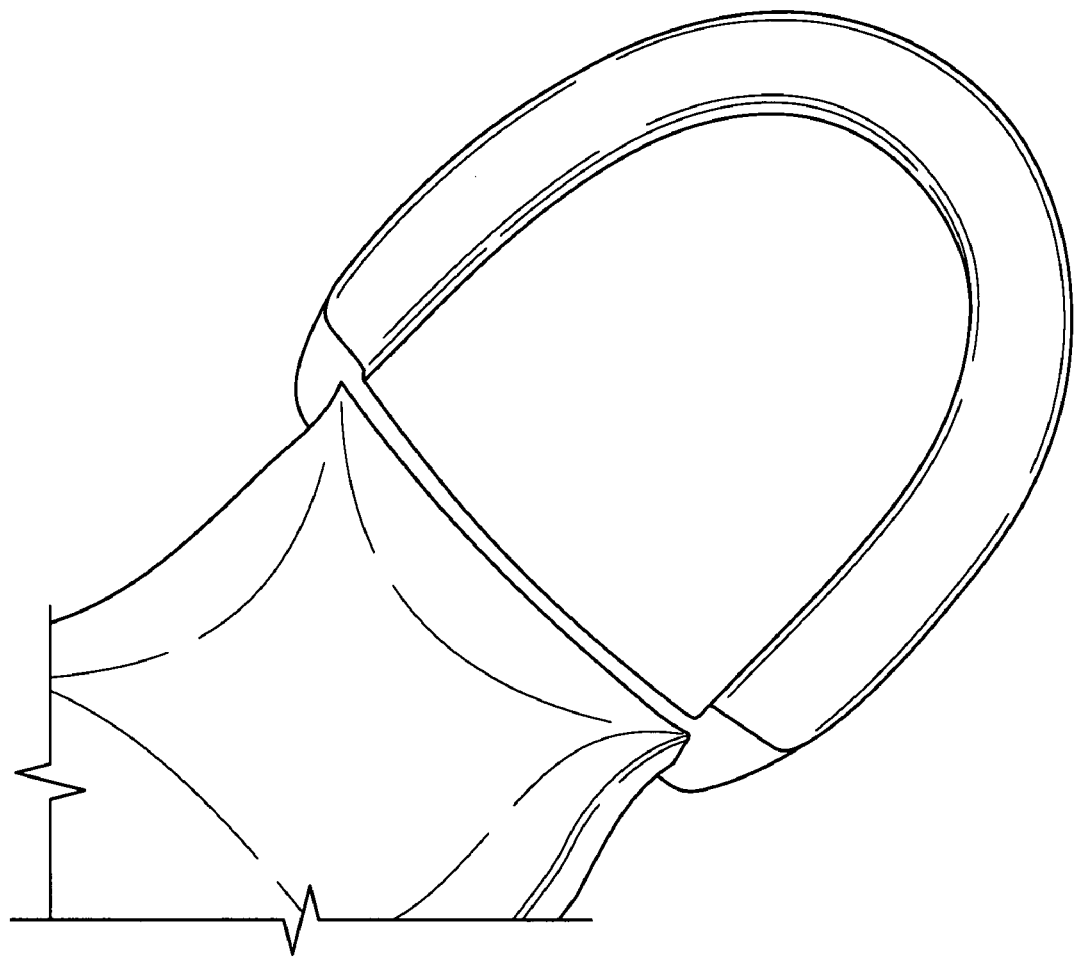
FIG. 16 shows an exemplary electrosurgical blade formed using the process described in FIGS. 15A and 15B.

When the insulation is applied over the cutting edge (which should be uninsulated for electrosurgical cutting), the insulation may be removed by grinding, abrading or by stimulation, as described above. FIGS. 15A and 15B illustrate a method of fabricating one variation of an electrosurgical blade. The blade illustrated in this exemplary method resembles the electrosurgical blade of FIGS. 14 and 16, however, this method may be varied to form other exemplary blades, as herein described.

In FIG. 15A, the blade region of the electrode is first cut 1501 from a thin piece of conductive material. The conductive material in this example is a foil. For example, a 7 mm×5 mm rectangle of 15 μm titanium foil is cut to form the active electrode, including the active edge of the electrode. The edges of this cut may be smoothed and de-burred with grinder. Next a shield or support that will attach to the blade is cut 1503. For example, the support may be cut with shears to a 19 mm×10 mm rectangle of 50 μm titanium foil, and the edges may be smoothed and de-burred with grinder. In this variation the support is a thicker or heavier conductive material. The support in this example is conductive so that it may help make an electrical contact with a connector (e.g., wire). The support/shield may then be formed by folding it in half, as shown. Thus, the 50 μm foil is folded in half along the 19 mm dimension to bring the 10 mm dimension to 5 mm. The folded support is then pressed with pliers to make the fold tight. The edge of the support is then cut to mirror the edge of the cutting electrode. In this example, at one 5 mm edge of the folded foil, approximately 1 mm is cut off the bent edge 7.5 mm along the 19 mm dimension so that the cut electrode can be sandwiched between these freed ends of the 50 μm foil, as shown 1505. Thus, the support is cut with shears and shaped with grinder so that one end of the 50 μm foil is rounded and has a 2 mm radius. The edges may then be de-burred.

The cut electrode is then inserted into the formed support 1507, and the edge of the electrode can be trimmed, leaving an overhang that will form the erodible depth behind the active edge of the electrode. In this example, the electrode (the 15 μm titanium foil) is cut with shears to a radius of 2.5 mm, and the edges again de-burr using grinder. The two foils may then be cleaned 1509. For example, they may be detached and placed in an ultrasonic cleaner for 5 minutes in 70% IPA to clean. The cleaned foils can then be put into an oven for drying (while venting) for 10 minutes at 100° C. The electrode and the support/shield can the be attached together 1511. For example, the working blade can be inserted into the support, and spot welded onto the surface of the 50 μm foil support in 7 points (e.g., 0.3 mm-0.5 mm from the edge), evenly and symmetrically along the edge line as shown.

Once the blade is connected to the shield/support, it may be insulated 1513. For example, a thin layer of Thomson glass enamel may be applied by dipping the assembly of the blade and support into enamel and letting it sit upright so that the enamel is evenly covering the blade. The assembly may be recoated if needed, so that the total thickness of the insulator is less than 3× the thickness of the electrode edge. To avoid applying too much insulator, do not recoat more than twice. In some variations, the viscosity or concentration of the enamel may be adjusted so that only the desired amount of insulator is applied.

After applying the enamel, it may be cured by placing it in the middle of the quartz tube in a furnace, and heated to 730° C. After cooling, the blade may be removed from the quartz tube holder for further processing (e.g., removal of the insulation from the edge and/or attachment to a handle or adapter).

Further processing of the electrode is shown in FIG. 15B, continuing after the insulation of the blade shown in FIG. 15A. Once the blade has been insulated, the electrode may be adapted to fit a handle or other attachment 1515. In this case, the lower portion of the electrodes (apart from the cutting edge) are trimmed and attached to a connector, such as a wire. For example, the lower part of the blade electrode may be trimmed to a 2 mm width for a length of 5-7 mm, as shown. The ends of a wire may then be stripped and attached to the electrode 1517. For example, a lead wire may be connected to the blade by wrapping the wire around the uncoated (uninsulated) area of the electrode. The wire may be fastened to the electrode by heat shrink tubing. The wire and electrode assembly may then be installed onto a handle 1519. For example, ¼" shrinking tube (~5 cm) may be used to secure the electrode to a handle with the lead wire exiting from the proximal end. The electrode assembly may then be sterilized, cleaned and/or packaged for later use. For example, the blade electrode assembly may be sterilized using Gamma radiation (e.g., for minimum of 25 kGy). The insulated cutting edge may be exposed before sterilizing and packaging (e.g., to remove the insulation along the cutting edge).

As mentioned above, fabrication of a blade having uniform erosion can be simplified by using the electrical discharge itself to remove the insulators from the cutting edge of the blade surfaces near the blade edge. For example, in some variations the active electrode of the blade is made from a foil having a thickness that is equivalent to what will be the edge thickness of the electrode (e.g., 15 μm). The foil may be mounded to a support structure so that the edge (and any adjacent etchable depth region) is exposed, and the foil (but especially the edge region and etchable depth) are completely coated with an insulator (e.g., glass). For example, the structure may be dipped into a coating solution of glass enamel so that that a layer of glass enamel covers the entire edge. However, in order to use the electrode, the cutting edge of the electrode must be uncovered so that it is not insulated. This may be efficiently done by applying pulses of energy to fracture and remove insulation from just the active edge.

Figure 17:
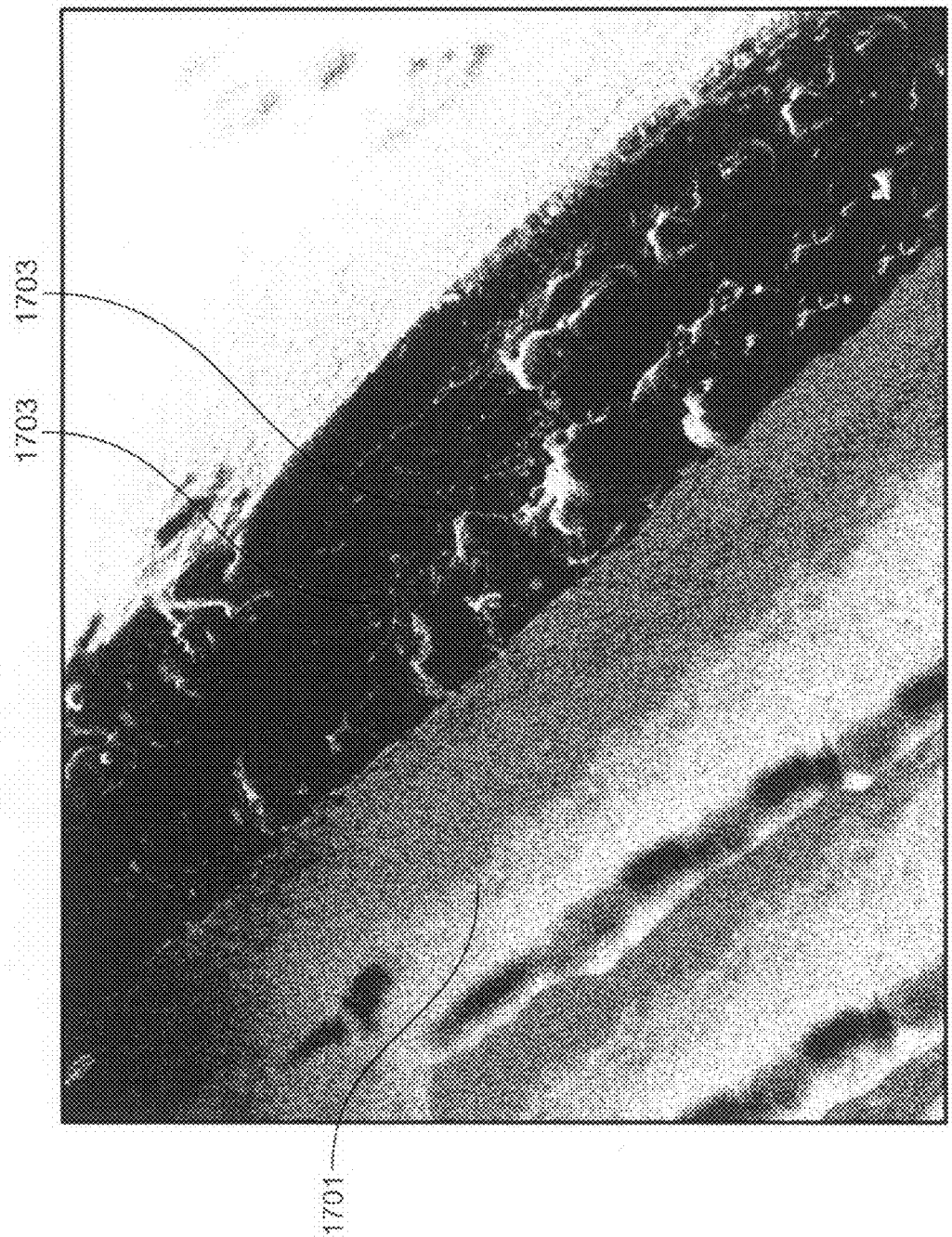
FIG. 17 is a scanning electron micrograph of an electrosurgical cutting electrode after electrical stimulation.

The active edge may be exposed by immersing the insulated blade (having a thickness of insulation that is less than 3× the thickness of the active edge) into a conductive medium applying electrical pulses with waveform parameters similar or identical to those appropriate for electrosurgery (e.g., as shown in FIGS. 13A-13E). The electrical discharge at the edge will break and remove the insulator from the active surfaces of the electrode, but in other areas the insulator will remain intact. As the blade edge is etched during use, the insulator in its proximity will be removed as well. This was schematically illustrated in FIG. 9, and can be shown by a scanning electron micrograph of an electrosurgical cutting electrode as shown in FIG. 17. In FIG. 17, the exposed titanium cutting electrode 1701 is surrounded on both sides by a layer of glass insulation 1703.

The above detailed description is provided to illustrate exemplary embodiments and is not intended to be limiting. For example, any of the features of an embodiment may be combined with some or all of the features of other embodiments. It will be apparent to those skilled in the art that numerous modifications and variations within the scope of the present invention are possible. Throughout this description, particular examples have been discussed, including descriptions of how these examples may address certain disadvantages in related art. However, this discussion is not meant to restrict the various examples to methods and/or systems that actually address or solve the disadvantages. Accordingly, the present invention is defined by the appended claims and should not be limited by the description herein.

What is claimed as new and desired to be protected by Letters Patent of the United States is:

1. An electrosurgical blade for use with an electrosurgical power supply, the blade comprising:
   an electrode having an insulated area and an exposed edge region, the exposed edge region having a thickness between about 1 μm and about 100 μm; and
   an insulator layer extending at least partially along the length of the electrode abutting and surrounding the exposed electrode edge region, and wherein the insulator layer has a thickness between about half to about three times the thickness of the exposed electrode edge region wherein the insulator layer is of a material matching a rate of erosion of the electrode during plasma formation along the electrode;
   wherein during the plasma formation the relative thicknesses of the exposed electrode edge region and the insulator layer remain constant as the exposed electrode edge region and insulator layer erode.

2. The electrosurgical blade of claim 1, wherein the electrode comprises a metal selected from the group consisting of titanium, tantalum, molybdenum, tungsten and stainless steel.

3. The electrosurgical blade of claim 1, wherein the electrode is formed from a metal foil having a thickness of about 10 μm to about 50 μm.

4. The electrosurgical blade of claim 1, wherein the insulator layer material comprises high temperature grade, lead-free glass enamel.

5. The electrosurgical blade of claim 1, wherein the insulated length of the electrode is greater than about 0.1 mm.

6. The electrosurgical blade of claim 1, wherein the length of the exposed electrode edge region is substantially straight.

7. The electrosurgical blade of claim 1, wherein the length of the exposed electrode edge region is curved.

8. The electrosurgical blade of claim 1, wherein the electrosurgical blade forms a scoop having the exposed electrode edge region disposed at the perimeter of the scoop.

9. The electrosurgical blade of claim 1, further comprising a handle interface configured to secure the electrosurgical blade to a handle so that the electrode may make electrical contact with the electrosurgical power supply.

10. The electrosurgical blade of claim 1, wherein the exposed electrode edge region forms a shape selected from the group consisting of an L-shape, U-Shape, V-shape, O-shape, or a combination of these shapes.

11. The electrosurgical blade of claim 1, wherein the exposed electrode edge region is configured to form a substantially uniform electrical field when power is supplied thereto by the electrosurgical power supply.

12. The electrosurgical blade of claim 1, wherein the insulator layer material is selected from the group consisting of glass and glass enamel.

13. The electrosurgical blade of claim 1, wherein the insulator layer material has a softening point or melting point above about 400° C.

14. An electrosurgical blade for use with an electrosurgical power supply, the blade comprising:
   a planar electrode having an upper and a lower surface, and an exposed edge region, wherein the upper and lower surfaces extend from the exposed electrode edge region by a length greater than about 100 μm, and wherein the upper and lower surfaces are separated by the electrode having a thickness between about 10 μm and 100 μm over this length; and a first insulation layer covering the upper surface, and a second insulation layer covering the lower surface, wherein the thickness of the first and second insulation layers is between about half and three times the electrode thickness wherein the first and second insulation layers are of a material matching a rate of erosion of the electrode during plasma formation along the electrode;

wherein during the plasma formation the relative thicknesses of the exposed electrode edge region and the first and second insulation layers remain constant as the exposed electrode edge region and the first and second insulation layers erode.

15. The electrosurgical blade of claim 14, wherein the planar electrode is formed from a conductive metal foil selected from the group consisting of titanium, tantalum, molybdenum, tungsten and stainless steel foils.

16. The electrosurgical blade of claim 14, wherein the first and second insulation layers material has softening point or melting point between about 400° C. and 900° C.

17. The electrosurgical blade of claim 14, wherein the first and second insulation layers material comprises glass enamel.

18. The electrosurgical blade of claim 14, wherein the first and second insulation layers material is selected from the group consisting of glass-and glass enamel.

19. An electrosurgical blade for use with a power supply, the blade comprising:

an electrode having an insulated length and an exposed edge region, the exposed edge region having a thickness between about 1 μm and about 100 μm; and an insulator layer extending at least partially along the length of the active electrode and abutting and surrounding the exposed electrode edge region, and wherein the insulator layer has a thickness between about half to about three times the thickness of the exposed electrode edge region wherein the insulator layer is of a material matching a rate of erosion of the electrode during plasma formation along the electrode;

wherein the exposed electrode edge region and the surrounding insulator layer define an edge profile, wherein during the plasma formation the relative thicknesses of the insulator layer and the exposed electrode edge region remain constant when the electrosurgical blade is activated by the electrosurgical power supply, substantially preserving the edge profile as the exposed electrode edge region and insulator layer erode.

20. The electrosurgical blade of claim 19, wherein the insulator layer material comprises glass.

21. The electrosurgical blade of claim 19, wherein the insulator layer material comprises lead-free enamel.

22. The electrosurgical blade of claim 19, wherein the electrode is formed of a metal foil, wherein the metal is selected from the group consisting of titanium, tantalum, molybdenum, tungsten and stainless steel.

23. The electrosurgical blade of claim 19, wherein the electrode is formed from foil approximately 15 μm thick.

24. The electrosurgical blade of claim 19 wherein the insulated length of the electrode is greater than about 0.1 mm.

25. The electrosurgical blade of claim 19, wherein the exposed edge region is substantially straight along its entire length.

26. The electrosurgical blade of claim 19, wherein the exposed electrode edge region is curved to form a shape selected from the group consisting of an L-shape, U-Shape, V-shape, O-shape, or a combination of these shapes.

27. The electrosurgical blade of claim 19, further comprising a handle interface configured to secure the electrosurgical blade to a handle so that the electrode may make electrical contact with the electrosurgical power supply.

* * * * *

UNITED STATES PATENT AND TRADEMARK OFFICE
CERTIFICATE OF CORRECTION

| | | |
|---|---|---|
| PATENT NO. | : 7,736,361 B2 | Page 1 of 1 |
| APPLICATION NO. | : 11/787500 | |
| DATED | : June 15, 2010 | |
| INVENTOR(S) | : Palanker et al. | |

It is certified that error appears in the above-identified patent and that said Letters Patent is hereby corrected as shown below:

In the Specification Under Column 1:

• Please replace Column 1, line no. 5-10 with:

-- FEDERALLY-SPONSORED RESEARCH OR DEVELOPMENT
This invention was made with Government support under contract EY012888 awarded by the National Institutes of Health. The Government has certain rights in this invention. --

Signed and Sealed this
Thirtieth Day of April, 2013

Teresa Stanek Rea
*Acting Director of the United States Patent and Trademark Office*